United States Patent
Bachnoff et al.

(10) Patent No.: US 10,745,452 B2
(45) Date of Patent: *Aug. 18, 2020

(54) COMBINATION OF ANTIMICROBIAL PEPTIDES AND ANTIBIOTIC DRUGS FOR TREATING DISEASES

(71) Applicant: OMNIX MEDICAL LTD., Jerusalem (IL)

(72) Inventors: Niv Bachnoff, Modiin (IL); Moshe Cohen-Kutner, Lotem (IL)

(73) Assignee: OMNIX MEDICAL LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/323,713

(22) PCT Filed: Aug. 7, 2017

(86) PCT No.: PCT/IL2017/050869
§ 371 (c)(1),
(2) Date: Feb. 6, 2019

(87) PCT Pub. No.: WO2018/029676
PCT Pub. Date: Feb. 15, 2018

(65) Prior Publication Data
US 2019/0177379 A1   Jun. 13, 2019

Related U.S. Application Data

(60) Provisional application No. 62/372,353, filed on Aug. 9, 2016.

(51) Int. Cl.
| | | |
|---|---|---|
| A61K 38/00 | (2006.01) | |
| C07K 14/435 | (2006.01) | |
| A61P 31/04 | (2006.01) | |
| A61K 38/17 | (2006.01) | |
| A61P 31/00 | (2006.01) | |
| A61K 31/407 | (2006.01) | |
| A61K 31/43 | (2006.01) | |
| A61K 31/65 | (2006.01) | |
| A61K 31/7036 | (2006.01) | |

(52) U.S. Cl.
CPC ...... *C07K 14/43563* (2013.01); *A61K 31/407* (2013.01); *A61K 31/43* (2013.01); *A61K 31/65* (2013.01); *A61K 31/7036* (2013.01); *A61K 38/1767* (2013.01); *A61P 31/00* (2018.01); *A61P 31/04* (2018.01); *Y02A 50/473* (2018.01); *Y02A 50/481* (2018.01); *Y02A 50/483* (2018.01)

(58) Field of Classification Search
CPC combination set(s) only.
See application file for complete search history.

(56) References Cited

U.S. PATENT DOCUMENTS

| | | |
|---|---|---|
| 5,990,273 A | 11/1999 | Andersson et al. |
| 2003/0092612 A1 | 5/2003 | Lyons |
| 2014/0142028 A1 | 5/2014 | Eckert et al. |
| 2014/0349917 A1 | 11/2014 | Eckert et al. |

FOREIGN PATENT DOCUMENTS

WO   2016132359   8/2016

OTHER PUBLICATIONS

Mataraci et al. "In vitro Activities of Antibiotics and Antimicrobial Cationic Peptides Alone and in Combination against Methicillin-Resistant *Staphlococcus aureus* Biofilms." Antimicrobial Agents and Chemotherapy, vol. 56, No. 12 (2012), pp. 6366-6371.
Bulet, et al (2005) Insect antimicrobial peptides: structures, properties and gene regulation, Protein and Peptide Letters, vol. 12, No. 1, pp. 3-11.
Bulet, et al (2004) Anti-microbial peptides: from invertebrates to vertebrates, Immunological Review, vol. 198, No. 1, pp. 169-184.
Bowman, et al (1987) Cell-Free Immunity in Insects, Annual Reviews Microbiology, vol. 41, pp. 103-126.
Bulet, et al (1999) Les peptides antimicrobiens de la drospophile, Medicine Sciences Paris, vol. 15, No. 1, pp. 23-29.
Bowman, et al (1991) Cell-Free Immunity in Cecropia. A model system for antibacterial proteins, European Journal of Biochemistry, vol. 201, No. 1, pp. 23-31.
Bowie, et al (1990) Deciphering the message in protein sequences: tolerance to amino acid substitutions, Science, vol. 247, No. 4948, pp. 1306-1310.
Booth, et al (1988) The use of a 'universal' yeast expression vector to produce an antigenic protein of Mycobacterium leprae, Immunology Letters, vol. 19, No. 1, pp. 65-70.
Fingl, et al (1975) The Pharmacological Basis of Therapeutics, Chapter 1, p. 1.
Gardella, et al (1990) Expression of Human Parathyroid Hormone-(1-84) in *Escherichia coli* as a Factor X-cleavable Fusion Protein, The Journal of Biological Chemistry, vol. 265, No. 26, pp. 15854-15859.
Hoffman, et al (1993) The humoral antibacterial response of *Drosophila*, Federation of European Biochemical Societies, Let, vol. 325, No. 1, 2, pp. 63-66.

(Continued)

*Primary Examiner* — Thomas S Heard
(74) *Attorney, Agent, or Firm* — The Roy Gross Law Firm, LLC; Roy Gross

(57) ABSTRACT

The invention provides a peptide comprising: a core amino acid sequence, which is identical or similar to the amino acid sequence of a member of the Cecropin family in a combination with an antibiotic drug.
The invention further provides methods of treating an infection, overcoming inherent or acquired resistance of a microorganism to an antibiotic agent or disinfecting a wound, the methods comprises administering the peptide in combination with the antibiotic drug to a subject in need thereof, wherein the peptide and the antibiotic drug are administered simultaneously or consecutively.

9 Claims, 3 Drawing Sheets

Specification includes a Sequence Listing.

(56) References Cited

OTHER PUBLICATIONS

Lockey, et al (1996) Formation of pores in *Escherichia coli* cell membranes by a cecropin isolated from hemolymph of Heliothis virescens larvae, FEBS, vol. 236(1), pp. 263-271.

Marassi, et al (1999) Orientation of Cecropin A Helices in Phospholipid Bilayers Determined by Solid-State NMR Spectroscopy, Biophysical Journal, vol. 77(6), pp. 3152-3155.

Morishima, et al (1990) Isolation and structure of cecropins, inducible antibacterial peptides, from the silkworm, *Bombyx mori*, Comparative Biochemistry and Physiology. B, Comparative Biochemistry, vol. 95, No. 2, pp. 551-554.

Steiner, et al (1981) Sequence and Specificity of Two Antibacterial Proteins Involved in Insect Immunity, Nature, The Journal of Immunology, vol. 292, No. 5820, pp. 246-248.

Sun, et al (1998) Peptide sequence of an antibiotic cecropin from the vector mosquito, *Aedes albopictus*, Biochemical and Biophysical Research Communications, vol. 249, No. 2, pp. 410-415.

Wang, et al (1998) The Dependence of Membrane Permeability by the Antibacterial Peptide Cecropin B and its Analogs, CB-1 and CB-3, on Liposomes of Different Composition, The Journal of Biological Chemistry, vol. 273, No. 42, pp. 27438-27444.

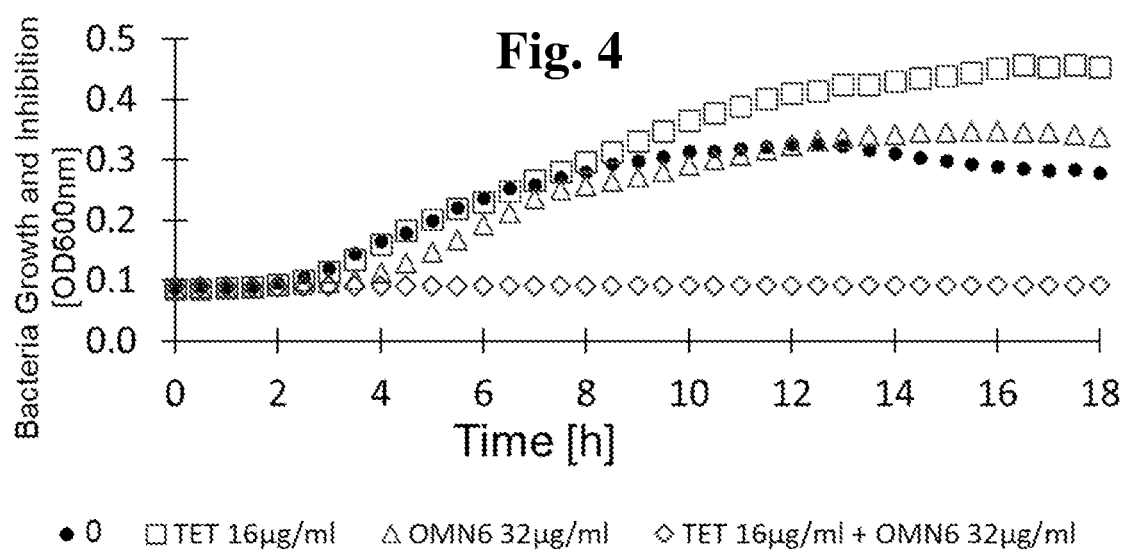

SEQUENCE LISTING

```
<160> NUMBER OF SEQ ID NOS: 33

<210> SEQ ID NO 1
<211> LENGTH: 43
<212> TYPE: PRT
<213> ORGANISM: Artificial Sequence
<220> FEATURE:
<223> OTHER INFORMATION: Artificial modified Cecropin protein

<400> SEQUENCE: 1

Met Cys Gly Trp Leu Lys Lys Ile Gly Lys Lys Ile Glu Arg Val Gly
1               5                   10                  15

Gln His Thr Arg Asp Ala Thr Ile Gln Gly Leu Gly Ile Ala Gln Gln
            20                  25                  30

Ala Ala Asn Val Ala Ala Thr Ala Arg Gly Cys
        35                  40

<210> SEQ ID NO 2
<211> LENGTH: 38
<212> TYPE: PRT
<213> ORGANISM: Artificial Sequence
<220> FEATURE:
<223> OTHER INFORMATION: Artificial modified Cecropin protein

<400> SEQUENCE: 2

Met Cys Lys Trp Lys Val Phe Lys Lys Ile Glu Met Lys Gly Arg Asn
1               5                   10                  15
```

```
Ile Arg Asn Gly Ile Val Lys Ala Gly Pro Ala Ile Ala Val Leu Gly
            20                  25                  30

Glu Ala Lys Ala Leu Cys
        35

<210> SEQ ID NO 3
<211> LENGTH: 39
<212> TYPE: PRT
<213> ORGANISM: Artificial Sequence
<220> FEATURE:
<223> OTHER INFORMATION: Artificial modified Cecropin protein

<400> SEQUENCE: 3

Met Cys Trp Asn Pro Phe Lys Glu Leu Glu Arg Ala Gly Gln Arg Val
1               5                   10                  15

Arg Asp Ala Val Thr Ser Ala Ala Pro Ala Val Ala Thr Val Gly Gln
            20                  25                  30

Ala Ala Ala Ile Ala Arg Cys
        35

<210> SEQ ID NO 4
<211> LENGTH: 39
<212> TYPE: PRT
<213> ORGANISM: Artificial Sequence
<220> FEATURE:
<223> OTHER INFORMATION: Artificial modified Cecropin protein

<400> SEQUENCE: 4

Met Cys Trp Asn Pro Phe Lys Glu Leu Glu Lys Val Gly Gln Arg Val
1               5                   10                  15

Arg Asp Ala Val Ile Ser Ala Gly Pro Ala Val Ala Thr Val Ala Gln
            20                  25                  30

Ala Thr Ala Leu Ala Lys Cys
        35

<210> SEQ ID NO 5
<211> LENGTH: 39
<212> TYPE: PRT
<213> ORGANISM: Artificial Sequence
<220> FEATURE:
<223> OTHER INFORMATION: Artificial modified Cecropin protein

<400> SEQUENCE: 5

Met Cys Trp Asn Pro Phe Lys Glu Leu Glu Arg Ala Gly Gln Arg Val
1               5                   10                  15

Arg Asp Ala Ile Ile Ser Ala Gly Pro Ala Val Ala Thr Val Ala Gln
            20                  25                  30

Ala Thr Ala Leu Ala Lys Cys
        35

<210> SEQ ID NO 6
<211> LENGTH: 40
<212> TYPE: PRT
<213> ORGANISM: Artificial Sequence
<220> FEATURE:
<223> OTHER INFORMATION: Artificial modified Cecropin protein

<400> SEQUENCE: 6

Met Cys Lys Trp Lys Leu Phe Lys Lys Ile Glu Lys Val Gly Gln Asn
1               5                   10                  15

Ile Arg Asp Gly Ile Ile Lys Ala Gly Pro Ala Val Ala Val Val Gly
            20                  25                  30
```

Gln Ala Thr Gln Ile Ala Lys Cys
        35                  40

<210> SEQ ID NO 7
<211> LENGTH: 38
<212> TYPE: PRT
<213> ORGANISM: Artificial Sequence
<220> FEATURE:
<223> OTHER INFORMATION: Artificial modified Cecropin protein

<400> SEQUENCE: 7

Met Cys Arg Trp Lys Ile Phe Lys Lys Ile Glu Lys Val Gly Gln Asn
1               5                   10                  15

Ile Arg Asp Gly Ile Val Lys Ala Gly Pro Ala Val Ala Val Val Gly
            20                  25                  30

Gln Ala Ala Thr Ile Cys
        35

<210> SEQ ID NO 8
<211> LENGTH: 38
<212> TYPE: PRT
<213> ORGANISM: Artificial Sequence
<220> FEATURE:
<223> OTHER INFORMATION: Artificial modified Cecropin protein

<400> SEQUENCE: 8

Met Cys Arg Trp Lys Ile Phe Lys Lys Ile Glu Lys Met Gly Arg Asn
1               5                   10                  15

Ile Arg Asp Gly Ile Val Ala Ala Gly Pro Ala Ile Glu Val Leu Gly
            20                  25                  30

Ser Ala Lys Ala Ile Cys
        35

<210> SEQ ID NO 9
<211> LENGTH: 38
<212> TYPE: PRT
<213> ORGANISM: Artificial Sequence
<220> FEATURE:
<223> OTHER INFORMATION: Artificial modified Cecropin protein

<400> SEQUENCE: 9

Met Cys Lys Trp Lys Ile Phe Lys Lys Ile Glu Lys Val Gly Arg Asn
1               5                   10                  15

Ile Arg Asn Gly Ile Ile Lys Ala Gly Pro Ala Val Ala Val Leu Gly
            20                  25                  30

Glu Ala Lys Ala Leu Cys
        35

<210> SEQ ID NO 10
<211> LENGTH: 42
<212> TYPE: PRT
<213> ORGANISM: Artificial Sequence
<220> FEATURE:
<223> OTHER INFORMATION: Artificial modified Cecropin protein

<400> SEQUENCE: 10

Met Cys Gly Trp Leu Lys Lys Ile Gly Lys Lys Ile Glu Arg Val Gly
1               5                   10                  15

Gln His Thr Arg Asp Ala Thr Ile Gln Gly Leu Gly Ile Ala Gln Gln
            20                  25                  30

Ala Ala Asn Val Ala Ala Thr Ala Arg Cys
        35                  40

```
<210> SEQ ID NO 11
<211> LENGTH: 34
<212> TYPE: PRT
<213> ORGANISM: Artificial Sequence
<220> FEATURE:
<223> OTHER INFORMATION: Artificial modified Cecropin protein

<400> SEQUENCE: 11

Met Cys Ser Trp Leu Ser Lys Thr Ala Lys Lys Leu Glu Asn Ser Ala
1               5                   10                  15

Lys Lys Arg Ile Ser Glu Gly Ile Ala Ile Ala Ile Gln Gly Gly Pro
            20                  25                  30

Arg Cys

<210> SEQ ID NO 12
<211> LENGTH: 40
<212> TYPE: PRT
<213> ORGANISM: Sarcophaga peregrina

<400> SEQUENCE: 12

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg Gly
        35                  40

<210> SEQ ID NO 13
<211> LENGTH: 35
<212> TYPE: PRT
<213> ORGANISM: Hyalophora cecropia

<400> SEQUENCE: 13

Lys Trp Lys Val Phe Lys Lys Ile Glu Met Lys Gly Arg Asn Ile Arg
1               5                   10                  15

Asn Gly Ile Val Lys Ala Gly Pro Ala Ile Ala Val Leu Gly Glu Ala
            20                  25                  30

Lys Ala Leu
        35

<210> SEQ ID NO 14
<211> LENGTH: 36
<212> TYPE: PRT
<213> ORGANISM: Manduca sexta

<400> SEQUENCE: 14

Trp Asn Pro Phe Lys Glu Leu Glu Arg Ala Gly Gln Arg Val Arg Asp
1               5                   10                  15

Ala Val Thr Ser Ala Ala Pro Ala Val Ala Thr Val Gly Gln Ala Ala
            20                  25                  30

Ala Ile Ala Arg
        35

<210> SEQ ID NO 15
<211> LENGTH: 36
<212> TYPE: PRT
<213> ORGANISM: Hyalophora cecropia

<400> SEQUENCE: 15

Trp Asn Pro Phe Lys Glu Leu Glu Lys Val Gly Gln Arg Val Arg Asp
1               5                   10                  15
```

Ala Val Ile Ser Ala Gly Pro Ala Val Ala Thr Val Ala Gln Ala Thr
            20                  25                  30

Ala Leu Ala Lys
        35

<210> SEQ ID NO 16
<211> LENGTH: 36
<212> TYPE: PRT
<213> ORGANISM: Antheraea pernyi

<400> SEQUENCE: 16

Trp Asn Pro Phe Lys Glu Leu Glu Arg Ala Gly Gln Arg Val Arg Asp
1               5                   10                  15

Ala Ile Ile Ser Ala Gly Pro Ala Val Ala Thr Val Ala Gln Ala Thr
            20                  25                  30

Ala Leu Ala Lys
        35

<210> SEQ ID NO 17
<211> LENGTH: 37
<212> TYPE: PRT
<213> ORGANISM: Hyalophora cecropia

<400> SEQUENCE: 17

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 18
<211> LENGTH: 35
<212> TYPE: PRT
<213> ORGANISM: Bombyx mori

<400> SEQUENCE: 18

Arg Trp Lys Ile Phe Lys Lys Ile Glu Lys Val Gly Gln Asn Ile Arg
1               5                   10                  15

Asp Gly Ile Val Lys Ala Gly Pro Ala Val Ala Val Val Gly Gln Ala
            20                  25                  30

Ala Thr Ile
        35

<210> SEQ ID NO 19
<211> LENGTH: 35
<212> TYPE: PRT
<213> ORGANISM: Bombyx mori

<400> SEQUENCE: 19

Arg Trp Lys Ile Phe Lys Lys Ile Glu Lys Met Gly Arg Asn Ile Arg
1               5                   10                  15

Asp Gly Ile Val Ala Ala Gly Pro Ala Ile Glu Val Leu Gly Ser Ala
            20                  25                  30

Lys Ala Ile
        35

<210> SEQ ID NO 20
<211> LENGTH: 35
<212> TYPE: PRT

<213> ORGANISM: Antheraea pernyi

<400> SEQUENCE: 20

```
Lys Trp Lys Ile Phe Lys Lys Ile Glu Lys Val Gly Arg Asn Ile Arg
1               5                   10                  15

Asn Gly Ile Ile Lys Ala Gly Pro Ala Val Ala Val Leu Gly Glu Ala
            20                  25                  30

Lys Ala Leu
        35
```

<210> SEQ ID NO 21
<211> LENGTH: 39
<212> TYPE: PRT
<213> ORGANISM: Drosophila melanogaster

<400> SEQUENCE: 21

```
Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35
```

<210> SEQ ID NO 22
<211> LENGTH: 31
<212> TYPE: PRT
<213> ORGANISM: Sus scrofa domesticus

<400> SEQUENCE: 22

```
Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30
```

<210> SEQ ID NO 23
<211> LENGTH: 129
<212> TYPE: DNA
<213> ORGANISM: Artificial Sequence
<220> FEATURE:
<223> OTHER INFORMATION: Artificial modified Cecropin DNA

<400> SEQUENCE: 23

```
atgtgcggct ggctgaaaaa aattggcaaa aaaattgaac gcgtgggcca gcatacccgc    60
gatgcgacca ttcagggcct gggcattgcg cagcaggcgg cgaacgtggc ggcgaccgcg   120
cgcggctgc                                                           129
```

<210> SEQ ID NO 24
<211> LENGTH: 117
<212> TYPE: DNA
<213> ORGANISM: Artificial Sequence
<220> FEATURE:
<223> OTHER INFORMATION: Artificial modified Cecropin DNA

<400> SEQUENCE: 24

```
atgtgcaaat ggaaagtgtt taaaaaaatt gaaaaaatgg ccgcaacat tcgcaacggc     60 attgtgaaag cgggcccggc gattgcggtg ctgggcgaag cgaaagcgct gggctgc      117
```

<210> SEQ ID NO 25
<211> LENGTH: 120
<212> TYPE: DNA
<213> ORGANISM: Artificial Sequence

```
<220> FEATURE:
<223> OTHER INFORMATION: Artificial modified Cecropin DNA

<400> SEQUENCE: 25
atgtgctgga acccgtttaa agaactggaa cgcgcgggcc agcgcgtgcg cgatgcggtg      60
attagcgcgg cgccggcggt ggcgaccgtg ggccaggcgg cggcgattgc gcgcggctgc     120

<210> SEQ ID NO 26
<211> LENGTH: 123
<212> TYPE: DNA
<213> ORGANISM: Artificial Sequence
<220> FEATURE:
<223> OTHER INFORMATION: Artificial modified Cecropin DNA

<400> SEQUENCE: 26
atgtgctgga acccgtttaa agaactggaa aaagtgggcc agcgcgtgcg cgatgcggtg      60
attagcgcgg gcccggcggt ggcgaccgtg gcgcaggcga ccgcgctggc gaaaggcaaa     120
tgc                                                                   123

<210> SEQ ID NO 27
<211> LENGTH: 117
<212> TYPE: DNA
<213> ORGANISM: Artificial Sequence
<220> FEATURE:
<223> OTHER INFORMATION: Artificial modified Cecropin DNA

<400> SEQUENCE: 27
atgtgctgga acccgtttaa agaactggaa cgcgcgggcc agcgcgtgcg cgatgcgatt      60
attagcgcgg gcccggcggt ggcgaccgtg gcgcaggcga ccgcgctggc gaaatgc        117

<210> SEQ ID NO 28
<211> LENGTH: 123
<212> TYPE: DNA
<213> ORGANISM: Artificial Sequence
<220> FEATURE:
<223> OTHER INFORMATION: Artificial modified Cecropin DNA

<400> SEQUENCE: 28
atgtgcaaat ggaaactgtt taaaaaaatt gaaaaagtgg ccagaacat tcgcgatggc       60 attattaaag cgggcccggc ggtggcggtg gtgggccagg cgacccagat tgcgaaaggc     120
tgc                                                                   123

<210> SEQ ID NO 29
<211> LENGTH: 114
<212> TYPE: DNA
<213> ORGANISM: Artificial Sequence
<220> FEATURE:
<223> OTHER INFORMATION: Artificial modified Cecropin DNA

<400> SEQUENCE: 29
atgtgccgct ggaaaatttt taaaaaaatt gaaaaagtgg ccagaacat tcgcgatggc       60 attgtgaaag cgggcccggc ggtggcggtg gtgggccagg cggcgaccat ttgc           114

<210> SEQ ID NO 30
<211> LENGTH: 120
<212> TYPE: DNA
<213> ORGANISM: Artificial Sequence
<220> FEATURE:
<223> OTHER INFORMATION: Artificial modified Cecropin DNA

<400> SEQUENCE: 30
```

```
atgtgccgct ggaaaatttt taaaaaaatt gaaaaaatgg gccgcaacat tcgcgatggc        60
attgtgaaag cgggcccggc gattgaagtg ctgggcagcg cgaaagcgat tggcaaatgc       120

<210> SEQ ID NO 31
<211> LENGTH: 114
<212> TYPE: DNA
<213> ORGANISM: Artificial Sequence
<220> FEATURE:
<223> OTHER INFORMATION: Artificial modified Cecropin DNA

<400> SEQUENCE: 31
atgtgcaaat ggaaaatttt taaaaaaatt gaaaaagtgg gccgcaacat tcgcaacggc        60
attattaaag cgggcccggc ggtggcggtg ctgggcgaag cgaaagcgct gtgc             114

<210> SEQ ID NO 32
<211> LENGTH: 138
<212> TYPE: DNA
<213> ORGANISM: Artificial Sequence
<220> FEATURE:
<223> OTHER INFORMATION: Artificial modified Cecropin DNA

<400> SEQUENCE: 32
atgtgcagcg aagcgggctg gctgaaaaaa attggcaaaa aaattgaacg cgtgggccag        60 catcccgcg atgcgaccat tcagggcctg ggcattgcgc agcaggcggc gaacgtggcg       120
gcgaccgcgc gcggctgc                                                    138

<210> SEQ ID NO 33
<211> LENGTH: 102
<212> TYPE: DNA
<213> ORGANISM: Artificial Sequence
<220> FEATURE:
<223> OTHER INFORMATION: Artificial modified Cecropin DNA

<400> SEQUENCE: 33
atgtgcagct ggctgagcaa aaccgcgaaa aaactggaaa acagcgcgaa aaaacgcatt        60
agcgaaggca ttgcgattgc gattcagggc ggcccgcgct gc                         102
```

COMBINATION OF ANTIMICROBIAL PEPTIDES AND ANTIBIOTIC DRUGS FOR TREATING DISEASES

RELATED APPLICATIONS

This application is a National Phase of PCT Patent Application No. PCT/IL2017/050869 having International filing date of Aug. 7, 2017, which claims the benefit of priority of U.S. Provisional Application No. 62/372,353 filed on Aug. 9, 2016. The contents of the above applications are all incorporated by reference as if fully set forth herein in their entirety.

FIELD OF INVENTION

The invention encompasses combination of antimicrobial peptides and antibiotic compounds, for therapeutic uses. The peptides are based on the Cecropin family which serves as potent antibacterial agents. The antibiotic compounds are standard antibiotic drugs found in clinical use today. The co-treatment of the peptides and the antibiotic compounds serves to lower the effective concentration and effective doses of the antibiotic drugs needed when treating bacterial infections.

BACKGROUND OF THE INVENTION

Antibiotics are chemical substances having the capacity, in a dilute solution, to kill or inhibit growth of microorganisms. Antibiotics that are sufficiently nontoxic to the host are used as chemotherapeutic agents to treat infectious diseases of humans, animals, and plants. The term was originally restricted to substances produced by microorganisms, but has been extended to include synthetic and semi-synthetic compounds of similar chemical activity.

Antibiotic drugs are commonly classified based on their chemical structure, mechanism of action, or spectrum of activity. Most antibiotics target bacterial functions or growth processes (Calderon C. B., et al., Antimicrobial Susceptibility Testing Protocols. 2007, CRC Press. Taylor & Frances group) that are not in common with eukaryotic organisms. The major families of antibiotic drugs can be classified as follows: Penicillins and Cephalosporins are antibiotic drugs that target the bacterial cell wall. Polymyxins target the bacterial cell membrane. Rifamycins, Lipiarmycins, Quinolones, and Sulfonamides interfere with essential bacterial enzymes. Macrolides, Lincosamides and Tetracyclines target protein synthesis (Finberg R. W., et al., Clin. Infect. Dis. 2004, 39 (9): 1314-20). Further categorization is based on their target specificity, and thus, narrow-spectrum antibacterial antibiotics target specific types of bacteria, whereas broad-spectrum antibiotics affect a wide range of bacteria.

Extensive and widespread use of antimicrobial drugs led to the emergence of resistant strains of microorganisms. These microorganisms are no longer susceptible to currently available antimicrobial drugs. In order to lower or prevent lethal infectious diseases and maintain public health, new antimicrobial agents are required. This forces researchers to pursue novel antibiotics, not yet resistant by bacteria.

Antimicrobial peptides (AMPs) are part of the armament that insects have developed to fight off pathogens. Although usually cationic, the primary structures of insect AMPs vary markedly. Members of the most frequent AMP families adopt an α-helical conformation in membrane-mimetic environments (Bulet P. et al., *Protein and Peptide Letters*, 2005, 12, 3-11).

Insects produce antibacterial peptides, which are secreted to their hemolymph, as an innate defense against pathogenic infections (Boman, H. G. et al., *Annu. Rev. Microbiol.*, 1987, 41, 103-126). Some insect species are capable of producing 10-15 different antibiotic peptides (Hoffman, J. A., et al., *FEBS Let.*, 1993, 325, 663-664). Each peptide has a complete different range of antibacterial action (Bulet, P. Medicine Sciences 1999.15, 23-29).

Cecropins were first isolated from the hemolymph of *Hyalophora cecropia*. Cecropins are small cationic peptides consisting 29-42 amino acid residues, found in the Diptera order (genus *Drosophila, Sarcophaga*) and Lepidoptera order (genus *Hyalophora, Manduca, Bombyx, Antheraea*). It should be mentioned that a Cecropin was isolated from porcine intestine (Boman, H. G., et al. Eur. J. Biochem. 1991. 201, 23-31; Morishima, I., et al. Biochem. Physiol. 1990. 95B, 551-554; Steiner, H., et al. Nature 1981. 292, 246-248; Sun, D., et al. Biochem. Biophys. Res. Commun. 1998. 249(2), 410-415; Bulet, P. et al Immunological Reviews. 2004. 198, 169-184). The known sequences for the major Cecropins show that the N-terminal parts are strongly basic while the C-terminal regions are neutral and contain long hydrophobic stretches. In all cases the Cecropins have an amidated C-terminal residue (Boman, H. G. et al., *Annu. Rev. Microbiol.*, 1987, 41, 103-126). Cecropins secondary structure forms two amphiphatic α-helixes which are able to penetrate the bacterial membrane. This ability is followed by membrane loss of ionic gradient balance leading to bacterial death (Christensen, B. C., et al. Proc. Natl. Acad. Sci. USA. 1988 83:1670-1674; Lockey, T. D., et al. Eur. J. Biochem. 1996. 236, 263-271; Marassi, F. M., et al. Biophys. J. 1999. 77, 3152-3155; Wang, W., et al. *J. Biol. Chem.* 1998. 273, (42) 27438-27448).

Cecropins are very similar molecules as half the amino acid substitutions are strictly conservative. Theoretical predictions and circular dichroism spectra indicate that these peptides can form nearly perfect amphipathic α-helices with charged groups on one longitudinal side and hydrophobic side residues on the opposite side. Proteins with amphipathic helices are often associated with membranes, and this secondary structure may be of importance for the membrane-disrupting activity of the Cecropins (Boman, H. G. et al., *Annu. Rev. Microbiol.*, 1987, 41, 103-126).

The structure of different sequences of peptides of the Cecropin family shows that they represent similar types of molecules. In addition to strongly basic N-terminal region and a long hydrophobic stretch in the C-terminal half, there are other typical conserved features such as: tryptophan at position 2, the single and double lysines at positions 5, 8 and 9 and arginine at position 12. It can be concluded that there must have been strong selection pressures that have conserved certain Cecropin sequences in different types of insects throughout evolution (Boman, H. G., et al. Eur. J. Biochem. 1991. 201, 23-31).

SUMMARY OF THE INVENTION

The invention provides a method of overcoming inherent or acquired resistance of a microorganism to an antibiotic agent, comprising administering to a subject in need a combination of a) a peptide comprising: a core amino acid sequence, which is identical or similar to the amino acid sequence of a member of the Cecropin family, wherein the core amino acid sequence is extended at the N-terminus by an N-terminal group and/or extended at the C-terminus by a C-terminal group; and wherein the N-terminal group and/or the C-terminal group are identical or different or null and are capable of forming a covalent bond so as to form a cyclic peptide or a homomultimer assembly via intermolecular covalent linkage; and b) An antibiotic drug; wherein the peptide and the antibiotic drug are added simultaneously or consecutively.

The invention further provides a method of treating an infection, the method comprising administering to a subject in need a combination of a peptide comprising: a) a core amino acid sequence, which is identical or similar to the amino acid sequence of a member of the Cecropin family, wherein the core amino acid sequence is extended at the N-terminus by an N-terminal group and/or extended at the C-terminus by a C-terminal group; and wherein the N-terminal group and/or the C-terminal group are identical or different or null and are capable of forming a covalent bond so as to form a cyclic peptide or a homomultimer assembly via intermolecular covalent linkage; and b) An antibiotic drug; wherein the peptide and the antibiotic drug are added simultaneously or consecutively.

In some embodiments of the invention, there is provided a method of disinfecting a wound comprising contacting the wound with a combination of: a) a peptide comprising: a core amino acid sequence, which is identical or similar to the amino acid sequence of a member of the Cecropin family, wherein the core amino acid sequence is extended at the N-terminus by an N-terminal group and/or extended at the C-terminus by a C-terminal group; and wherein the N-terminal group and/or the C-terminal group are identical or different or null and are capable of forming a covalent bond so as to form a cyclic peptide or a homomultimer assembly via intermolecular covalent linkage; and b) An antibiotic drug; wherein the peptide and the antibiotic drug are added simultaneously or consecutively.

In some embodiments of the invention, there is provided a pharmaceutical composition comprising a combination of a peptide comprising: a core amino acid sequence, which is identical or similar to the amino acid sequence of a member of the Cecropin family, wherein the core amino acid sequence is extended at the N-terminus by an N-terminal group and/or extended at the C-terminus by a C-terminal group; and wherein the N-terminal group and/or the C-terminal group are identical or different or null and are capable of forming a covalent bond so as to form a cyclic peptide or a homomultimer assembly via intermolecular covalent linkage; and an antibiotic drug.

The invention further provides genetically engineered or synthesized degradation-resistant, peptides to be added simultaneously or consecutively, either before or after, an antibiotic drug. The peptide and the antibiotic drug may be added in a combined pharmaceutical composition or in separate two or more pharmaceutical compositions. In some embodiments, the peptides comprise at least one cysteine residue at their carboxy- and amino-terminus. In some embodiments of the invention, under oxidative environment, e.g. as in various infections, the cysteines in the carboxy- and amino-terminus of the peptides of the invention, are covalently bonded, thus creating in an embodiment of the invention a cyclic form of the peptides, wherein said cyclic peptides represent higher stability while maintaining its original biological activity.

Some embodiments of the invention are directed to a peptide comprising a core amino acid sequence, which is identical or similar to the amino acid sequence of a member of the Cecropin family, wherein the core amino acid sequence is extended at the N-terminus by an N-terminal group and/or extended at the C-terminus by a C-terminal group; and wherein the N-terminal group and/or the C-terminal group are identical or different and are capable of forming a covalent bond so as to form a cyclic peptide or a homomultimer assembly via intermolecular covalent linkage.

In some embodiments of the invention, the member of the Cecropin family belongs to the group of AMP $CM_{IV}$, Cecropin A, Cecropin B, Cecropin B2, Cecropin D, Cecropin IA, and Cecropin P1.

In some embodiments of the invention, the cyclic peptide has a topology, wherein the topology is head-to-tail, side-chain-to-side-chain, head-to-side-chain or side-chain-to-tail or backbone-to-backbone or side-chain-to-backbone or head-to-backbone or tail-to-backbone.

In some embodiments of the invention, the covalent linkage is formed under oxidative and/or acidic physiological conditions.

In some embodiments of the invention, the amino acid sequence of the member of the Cecropin family comprises 17-144 amino acids.

In some embodiments of the invention, the core amino acid sequence of a member of the Cecropin family is as set forth in SEQ ID Nos. 12-22.

In some embodiments of the invention, the core amino acid sequence has at least 70%, 75%, 80%, 85%, 90%, 95% or 99% sequence identity to the amino acid sequences set forth in SEQ ID Nos. 12-22.

In some embodiments of the invention, the core amino acid sequence comprising substitution, conservative amino acid substitutions, conservatively modified sequence variants, deletion, and/or insertion at one or more position.

In some embodiments of the invention, the C-terminus group and/or the N terminus group comprises one or more of cysteine, cysteine derivative, an amino acid sequence, which contains cysteine or a group comprising a thiol moiety or any combination thereof.

In some embodiments of the invention, the C-terminus group and/or the N terminus group are each selected from the group consisting of cysteine, cysteine derivative, an amino acid sequence which contains cysteine or any other group comprising a thiol moiety.

In some embodiments of the invention, the N-terminus group comprises the amino acid sequence methionine-cysteine, methionine-cysteine derivative, methionine derivative-cysteine or methionine derivative-cysteine derivative and the C-terminus group is cysteine or a cysteine derivative.

In some embodiments of the invention, the C-terminus group comprises the amino acid sequence methionine-cysteine, methionine-cysteine derivative, methionine derivative-cysteine or methionine derivative-cysteine derivative and the N-terminus group is cysteine or a cysteine derivative In some embodiments of the invention, the covalent linkage is a disulfide bond.

In some embodiments of the invention, the covalent linkage is an amide, lactam or peptide bond.

In some embodiments of the invention, the N-terminus group and the C-terminus group are covalently bound so as to form a cyclic peptide.

In some embodiments of the invention, the peptide is self-assembled within a physiological membrane such that the intermolecular covalent linkage is formed between the N-terminus group of the peptide to the N-terminus or a C-terminus group of an additional identical peptide or wherein the intermolecular covalent linkage is formed between the C-terminus group of the peptide to the N-terminus or a C-terminus groups of an additional identical peptide.

In some embodiments of the invention, the peptide is as set forth in any one of SEQ ID Nos. 1-11.

In some embodiments of the invention, the peptide has an amino acid sequence which is at least 70%, 75%, 80%, 85%, 90%, 95% or 99% sequence identity to the amino acid sequences set forth in SEQ ID Nos. 1-11.

In some embodiments of the invention, the peptide is as set forth in SEQ ID NO: 6.

In some embodiments of the invention, the peptide has an amino acid sequence which is at least 70%, 75%, 80%, 85%, 90%, 95% or 99% sequence identity to the amino acid sequence set forth in SEQ ID NO: 6.

The present invention relates to a nucleic acid sequence encoding any one of the above referenced peptides.

The present invention relates to a vector comprising the above referenced nucleic acid.

The present invention relates to a pharmaceutical composition comprising any one of the above referenced peptides or the above referenced nucleic acid.

The present invention relates to a pharmaceutical composition comprising any one of the above referenced peptides or the above referenced nucleic acid in conjugation with an antibiotic active compound.

The present invention relates to a method of treating an infection, the method comprising administering and one of the above referenced peptides or the above referenced pharmaceutical composition to a subject in need thereof.

The present invention relates to a use of any one of the above referenced peptides or the above referenced pharmaceutical composition in the preparation of a medicament for treating an infection in a subject.

The present invention relates to the use of one or more of the peptides of the invention administered in conjunction with one or more additional antibiotic compounds such as but not limited to: Penicillins, Cephalosporins, Polymyxins, Rifamycins, Lipiarmycins, Quinolones, Sulfonamides, Macrolides, Lincosamides and Tetracyclines, as a medicament for treating an infection in a subject.

In some embodiments of the invention, the infection is bacterial, viral- and/or fungal infection.

In some embodiments of the invention, the pharmaceutical composition is in a form of a liquid, cream, gel, paste, powder, emulsion, an ointment, a liniment, a lotion, a transdermal system, an injection fluid, a suspension, a patch film patch or spray.

In some embodiments of the invention, the pharmaceutical composition is in the form of capsule or a tablet.

In some embodiments of the invention, the composition or the peptide is administered in conjunction with one or more additional anti-inflammatory active agents, which may be an antibiotic drug.

The present invention relates to a method of overcoming inherent or acquired resistance of a microorganism to an antibiotic agent, comprising: contacting the microorganism to any one of the above referenced peptides or the above referenced pharmaceutical composition together with an antibiotic drug.

In some embodiments of the invention, the microorganism is *Escherichia coli, Klebsiella Pneumoniaea, Pseudomonas aeruginosa, Salmonella* serotype *Typhi, Acinetobacter baumannii*, a member of Enterobacteriaceae spp., *Pseudomonas* spp. *Salmonella* spp., or *Acinetobacter* spp., or any combination thereof.

The present invention relates to a method of disinfecting a wound comprising contacting the wound with any one of the above referenced peptides or the above referenced pharmaceutical composition together with an antibiotic drug.

In some embodiments of the invention, the wound is a blister wound, a soft tissue wound, a cutaneous abscess, a surgical wound, a sutured laceration, a contaminated laceration, a burn wound, a decubitus ulcer, a stasis ulcer, a leg ulcer, a foot ulcer, a venous ulcer, a diabetic ulcer, an ischemic ulcer, a pressure ulcer, an oral infection, a periodontal disease, a partial thickness burn, or a full thickness burn.

BRIEF DESCRIPTION OF THE FIGURES

FIG. 4: *Salmonella* serotype *Typhimurium* (ATCC 700408) bacteria growth was monitored over 17.5 hours via absorbance at 600 nm. Bacteria growth or inhibition of growth is presented as absorbance values at 600 nm over time (OD600 nm). As the bacteria grow, OD values increase. The combination of OMN6 and the antibiotic drug Tetracycline (TET) exerted a powerful antimicrobial effect that is demonstrated by the low and constant OD values that represent bacterial death.

DETAILED DESCRIPTION OF THE EMBODIMENTS OF THE INVENTION

Figure 1:
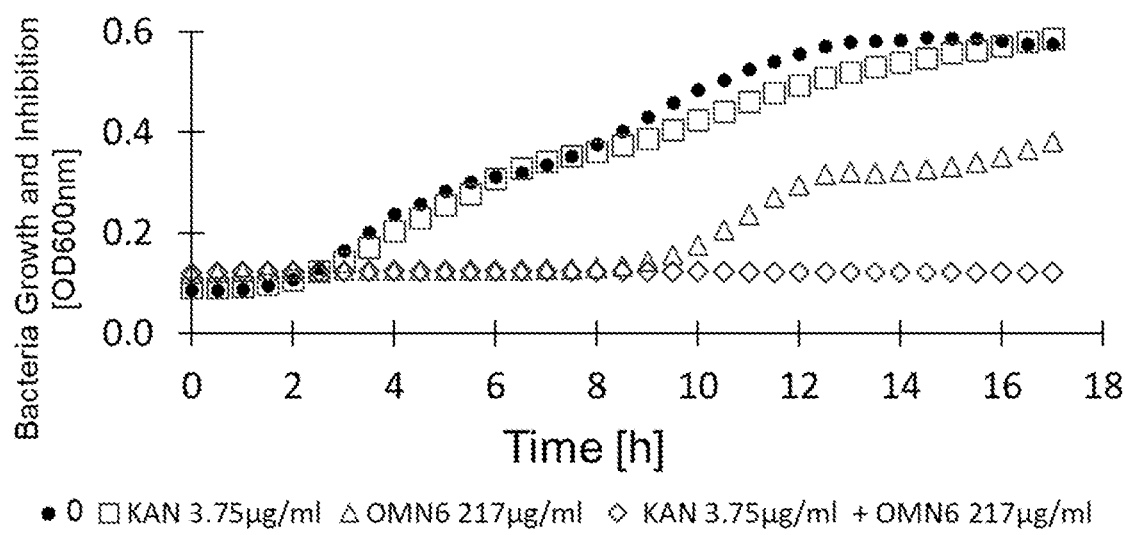
FIG. 1: *Salmonella* serotype *Typhimurium* (ATCC 700408) bacteria growth was monitored over 17.5 hours via absorbance at 600 nm. Bacteria growth or inhibition of growth is presented as absorbance values at 600 nm over time (OD600 nm). As the bacteria grow, OD values increase. The combination of OMN6 and the antibiotic drug Kanamycin (KAN) exerted a powerful antimicrobial effect that is demonstrated by the low and constant OD values that represent bacterial death.

The invention is based on peptides from the Cecropin family, which are expressed mainly in insects from the Lepidoptera and Diptera orders which are modified as described herein and are administered in combination with antibiotic drugs for treating disease or infections.

Some bacteria develop resistance to antibiotics through the expression of specialized pumps that upon activation lead to an efflux of drugs outside of the bacteria cells. The concentration of the antibiotic drug cannot reach effective levels intracellularly and the resistant bacteria stays alive. This form of resistance can be overcome if the influx of the antibiotic drug exceeds the efflux created by the pumps, leading to effective concentration of the antibiotic drug inside the bacteria cells. OMN antimicrobial peptides in some embodiments, form pores in the membranes of bacteria, these pores may increase the influx of any small-molecule-based antibiotic drug that is found in the surrounding media of the bacteria. This increased influx of the antibiotic drug may restore the effective concentration of the drug intracellularly and lead to the bacteria death.

The experiments described in the Examples Section demonstrate that when bacteria develop resistance to a specific drug, this drug is no longer effective even at high concentrations. This drug can no longer be used for therapeutic purposes as it has lost its ability to kill the resistant bacteria. In cases where an antibiotic drug is no longer effective against a resistant strain of bacteria, a combination of this drug with one of the peptides of the invention and in particular of those shown in Seq ID Nos. 1-11 can restore the ability of the drug to combat resistant bacteria. The present invention provides a method treating infection comprising administering peptides as described herein in combination with an antibiotic compound.

In some embodiments, the method of treating by using the combination of the peptides of the invention together with an antibiotic drug results in a synergistic antimicrobial effect which is stronger than a stand-alone treatment with either the antibiotic compound or the peptide described herein.

In some embodiments of the invention the peptide and or the antibiotic drug are applied in concentrations that when applied as stand-alone treatment, both the peptide and the antibiotic compound have not been shown effective.

The present invention provides degradation-resistant, peptides that can be used as antibiotic medicaments which may be applied alone or in combination with an antibiotic drug. In some embodiments, the peptide of the invention and the antibiotic drug may be administered together. In some embodiments, the peptide of the invention and the antibiotic drug are administered in the same formulation, which may be administered topically, by injection or orally, together with a pharmaceutical acceptable carrier. In some embodiments, the peptide of the invention and the antibiotic drug may be administered simultaneously, sequentially or one may use the peptide of the invention to treat an infection and add the antibiotic drug after more than one hour, more than two hours, more than five hours, more than 10 hours, more than 18 hours, more than a day, more than two days or more than a week.

The antibiotic drug may be any antibiotic drug. In some embodiments, the antibiotic drug is kanamycin, imipenem, ampicillin, tetracycline or any combination thereof. In some embodiments of the invention, the antibiotic drug is tetracycline, oxytetracycline, chlorotetracycline, demeclocycline, meclocycline, rolitetracycline, 6-thiatetracycline, 4-epi-anhydrochlortetracycline, aminomethylcycline, azatetracycline, fluorocycline, pentacycline, minocycline, doxycycline or tigecycline or any combination thereof.

In some embodiments of the invention the antibiotic drug is a beta-lactam antibiotic selected from the group consisting of penicillins, cephalosporins, cephamycins, carbapenems, ceftazidime, cefotaxime, ceftriaxone, cefpodoxime, and aztreonam.

In some embodiments of the invention the antibiotic drug can be selected one or more of the following groups Aminoglycoside, Ansamycin, Glycopeptide, Lincosamide, Macrolide, Monobactam, Nitrofuran, Oxazolidinone, Quinolone/Fluoroquinolone, Sulfonamide and Tetracycline.

In some embodiments, the method or the pharmaceutical composition of the invention are used in a subject that has antibiotic resistant bacterial infections caused by Gram-positive and/or Gram-negative bacterial pathogens. In some embodiments, the peptides comprise at least one cysteine residue at their carboxy- and amino-terminus. In some embodiments of the invention, under oxidative environment, e.g. as in various infections, the cysteines in the carboxy- and amino-terminus of the peptides of the invention, are covalently bonded, thus creating a cyclic form of the peptides, wherein said cyclic peptides represent higher stability while maintaining its original biological activity.

In some embodiments, there is provided a peptide comprising: a core amino acid sequence, which is identical or similar to the amino acid sequence of a member of the Cecropin family, wherein the core amino acid sequence is extended at the N-terminus by an N-terminal group and/or extended at the C-terminus by a C-terminal group; and wherein the N-terminal group and/or the C-terminal group are identical or different or null and are capable of forming a covalent bond so as to form a cyclic peptide or a homo-multimer assembly via intermolecular covalent linkage.

As used herein, in one embodiment the phrase "homo-multimer assembly" refers to molecular structural organization comprising more than one replica of the same molecule. The connectivity and structural organization of the different replicas of the same molecule could be maintained via covalent bond and/or non-covalent interactions.

As used herein, in one embodiment the phrase "intermolecular covalent linkage" refers to covalent bond that is formed between two identical or different molecules.

In some exemplary embodiments of the invention, the member of the Cecropin family belongs to the group of AMP CMIV, Cecropin A, Cecropin B, Cecropin B2, Cecropin D, Cecropin IA, and Cecropin P1.

Reference is made to Tables 1, 2 and 3 which show a library of 11 exemplary antimicrobial peptides of the invention (sequences 1-11, Table 1), the original sequences from the Cecropin family (sequences 12-22, Table 2), and nucleic acid sequences encoding the peptides as set forth in SEQ ID Nos. 1-11, Table 3).

Table 1 presents the amino acid sequence of the modified peptides. Inserted cysteine and methionine residues appear in bold.

TABLE 1

Omnix Medical Modified Peptides

| Name | Sequence ID | Species origin/ Original Cecropin | Amino acid sequence |
|---|---|---|---|
| OMN 1 | SEQ ID NO: 1 | *S. peregrina* Cecropin IA | MCGWLKKIGKKIERVGQHTRDA TIQGLGIAQQAANVAATARGC |
| OMN 2 | SEQ ID NO: 2 | *H. cecropia* Cecropin B | MCKWKVFKKIEMKGRNIRNGIV KAGPAIAVLGEAKALC |
| OMN 3 | SEQ ID NO: 3 | *M. sexta* Cecropin B-2 | MCWNPFKELERAGQRVRDAVTS AAPAVATVGQAAAIARC |
| OMN 4 | SEQ ID NO: 4 | *H. cecropia* Cecropin D | MCWNPFKELEKVGQRVRDAVIS AGPAVATVAQATALAKC |
| OMN 5 | SEQ ID NO: 5 | *A. pernyi* Cecropin D | MCWNPFKELERAGQRVRDAIISA GPAVATVAQATALAKC |
| OMN 6 | SEQ ID NO: 6 | *H. cecropia* Cecropin A | MCKWKLFKKIEKVGQNIRDGIIK AGPAVAVVGQATQIAKC |
| OMN 7 | SEQ ID NO: 7 | *B. mori* AMP $CM_{IV}$ | MCRWKIFKKIEKVGQNIRDGIVK AGPAVAVVGQAATIC |
| OMN 8 | SEQ ID NO: 8 | *B. mori* Cecropin A | MCRWKIFKKIEKMGRNIRDGIVA AGPAIEVLGSAKAIC |
| OMN 9 | SEQ ID NO: 9 | *A. pernyi* Cecropin B | MCKWKIFKKIEKVGRNIRNGIIK AGPAVAVLGEAKALC |
| OMN 10 | SEQ ID NO: 10 | *D. melanogaster* Cecropin A | MCGWLKKIGKKIERVGQHTRDA TIQGLGIAQQAANVAATARC |
| OMN 11 | SEQ ID NO: 11 | *S.s. domesticus* Cecropin P1 | MCSWLSKTAKKLENSAKKRISE GIAIAIQGGPRC |

Table 2 presents the amino acid sequences of exemplary peptides from the Cecropin family and their origin.

TABLE 2

Cecropin Family of Peptides

| Sequence ID | Species origin | Original Cecropin | Amino acid sequence |
|---|---|---|---|
| SEQ ID NO: 12 | *S. peregina* | Cecropin IA | GWLKKIGKKIERVGQHTRDA TIQGLGIAQQAANVAATARG |
| SEQ ID NO: 13 | *H. cecropia* | Cecropin B | KWKVFKKIEMKGRNIRNGIV KAGPAIAVLGEAKAL |
| SEQ ID NO: 14 | *M. sexta* | Cecropin B-2 | WNPFKELERAGQRVRDAVTS AAPAVATVGQAAAIAR |
| SEQ ID NO: 15 | *H. cecropia* | Cecropin D | WNPFKELEKVGQRVRDAVIS AGPAVATVAQATALAK |
| SEQ ID NO: 16 | *A. pernyi* | Cecropin D | WNPFKELERAGQRVRDAIIS AGPAVATVAQATALAK |
| SEQ ID NO: 17 | *H. cecropia* | Cecropin A | KWKLFKKIEKVGQNIRDGII KAGPAVAVVGQATQIAK |
| SEQ ID NO: 18 | *B. mori* | AMP $CM_{IV}$ | RWKIFKKIEKVGQNIRDGIV KAGPAVAVVGQAATI |
| SEQ ID NO: 19 | *B. mori* | Cecropin A | RWKIFKKIEKMGRNIRDGIV AAGPAIEVLGSAKAI |
| SEQ ID NO: 20 | *A. pernyi* | Cecropin B | KWKIFKKIEKVGRNIRNGIIK AGPAVAVLGEAKAL |

TABLE 2-continued

Cecropin Family of Peptides

| Sequence ID | Species origin | Original Cecropin | Amino acid sequence |
|---|---|---|---|
| SEQ ID NO: 21 | D. melanogaster | Cecropin A | GWLKKIGKKIERVGQHTRDA TIQGLGIAQQAANVAATAR |
| SEQ ID NO: 22 | S.s. domesticus | Cecropin P1 | SWLSKTAKKLENSAKKRISE GIAIAIQGGPR |

Table 3 presents the nucleic acid sequences encoding respectively the peptides of sequences 1-11.

TABLE 3

Nucleotide Sequence encoding the modified peptides of the invention.

| Name | Sequence ID | Species origin/ Original Cecropin | Nucleotide sequence |
|---|---|---|---|
| OMN 1 | SEQ ID NO: 23 | S. peregrina Cecropin IA | atgtgcggctggctgaaaaaaattggc aaaaaaattgaacgcgtgggccagcat acccgcgatgcgaccattcagggcctg ggcattgcgcagcaggcggcgaacgtg gcggcgaccgcgcgcggctgc |
| OMN 2 | SEQ ID NO: 24 | H. cecropia Cecropin B | atgtgcaaatggaaagtgtttaaaaaa attgaaaaaatgggccgcaacattcgc aacggcattgtgaaagcgggcccggcg attgcggtgctgggcgaagcgaaagcg ctgggctgc |
| OMN 3 | SEQ ID NO: 25 | M. sexta Cecropin B-2 | atgtgctggaacccgtttaaagaactg gaacgcgcgggccagcgcgtgcgcgat gcggtgattagcgcggcgccggcggtg gcgaccgtgggccaggcggcggcgatt gcgcgcggctgc |
| OMN 4 | SEQ ID NO: 26 | H. cecropia Cecropin D | atgtgctggaacccgtttaaagaactg gaaaaagtgggccagcgcgtgcgcgat gcggtgattagcgcgggcccggcggtg gcgaccgtggcgcaggcgaccgcgctg gcgaaaggcaaatgc |
| OMN 5 | SEQ ID NO: 27 | A. pernyi Cecropin D | atgtgctggaacccgtttaaagaactg gaacgcgcgggccagcgcgtgcgcgat gcgattattagcgcgggcccggcggtg gcgaccgtggcgcaggcgaccgcgctg gcgaaatgc |
| OMN 6 | SEQ ID NO: 28 | H. cecropia Cecropin A | atgtgcaaatggaaactgtttaaaaaa attgaaaaagtgggccagaacattcgc gatggcattattaaagcgggcccggcg gtggcggtggtgggccaggcgacccag attgcgaaaggctgc |
| OMN 7 | SEQ ID NO: 29 | B. mori AMP $CM_{IV}$ | atgtgccgctggaaaattttaaaaaa attgaaaaagtgggccagaacattcgc gatggcattgtgaaagcgggcccggcg gtggcggtggtgggccaggcggcgacc atttgc |
| OMN 8 | SEQ ID NO: 30 | B. mori Cecropin A | atgtgccgctggaaaattttaaaaaa attgaaaaaatgggccgcaacattcgc gatggcattgtgaaagcgggcccggcg attgaagtgctgggcagcgcgaaagcg attggcaaatgc |
| OMN 9 | SEQ ID NO: 31 | A. pernyi Cecropin B | atgtgcaaatggaaaattttaaaaaa attgaaaaagtgggccgcaacattcgc aacggcattattaaagcgggcccggcg gtggcggtgctgggcgaagcgaaagcg ctgtgc |

TABLE 3-continued

Nucleotide Sequence encoding the modified peptides of the invention.

| Name | Sequence ID | Species origin/ Original Cecropin | Nucleotide sequence |
|---|---|---|---|
| OMN 10 | SEQ ID NO: 32 | D. melanogaster Cecropin A | atgtgcagcgaagcgggctggctgaaa aaaattggcaaaaaaattgaacgcgtg ggccagcatacccgcgatgcgaccatt cagggcctgggcattgcgcagcaggcg gcgaacgtggcggcgaccgcgcgcggc tgc |
| OMN 11 | SEQ ID NO: 33 | S.s. domesticus Cecropin P1 | atgtgcagctggctgagcaaaaccgcg aaaaaactggaaaacagcgcgaaaaaa cgcattagcgaaggcattgcgattgcg attcagggcggcccgcgctgc |

In some embodiments of the invention, the cyclic peptide has a topology, wherein the topology is head-to-tail, side-chain-to-side-chain, head-to-side-chain or side-chain-to-tail or backbone-to-backbone or side-chain-to-backbone or head-to-backbone or tail-to-backbone. The cyclic peptide according to some embodiments of the invention is homodetic cyclic peptide, cyclic isopeptide, cyclic depsipeptide or bicyclic peptide. In some embodiments, the covalent linkage is formed under oxidative and/or acidic physiological conditions. In some embodiments, the peptide of the invention is a stapled peptide.

As used herein, in one embodiment relating to the topology of the cyclic peptide, the phrase "head-to-tail" refer to cyclization of the peptide via amide bond formation between the amino terminus and the carboxyl terminus of the peptide.

As used herein, in one embodiment relating to the topology of the cyclic peptide, the phrase "side-chain-to-side-chain" refers to cyclization of the peptide via the formation of covalent bond between two side chains.

As used herein, in one embodiment relating to the topology of the cyclic peptide, the phrase "head-to-side-chain" refers to cyclization of the peptide via the formation of covalent bond between the amino terminus and a side chain of the peptide.

As used herein, in one embodiment relating to the topology of the cyclic peptide, the phrase "side-chain-to-tail" refers to cyclization of the peptide via the formation of covalent bond between the carboxyl terminus and a side chain of the peptide.

As used herein, in one embodiment relating to the topology of the cyclic peptide, the phrase "backbone-to-backbone" refers to cyclization of the peptide via the formation of covalent bond between two different backbone atoms of the peptide.

As used herein, in one embodiment relating to the topology of the cyclic peptide, the phrase "side-chain-to-backbone" refers to cyclization of the peptide via the formation of covalent bond between a side chain and a backbone atom of the peptide.

As used herein, in one embodiment relating to the topology of the cyclic peptide, the phrase "head-to-backbone" refers to cyclization of the peptide via the formation of covalent bond between the amino terminus and a backbone atom of the peptide.

As used herein, in one embodiment relating to the topology of the cyclic peptide, the phrase "tail-to-backbone" refers to cyclization of the peptide via the formation of covalent bond between the carboxyl terminus and a backbone atom of the peptide.

In some embodiments, the core amino acid sequence of a member of the Cecropin family is as set forth in SEQ ID Nos: 12-22 as detailed in Table 2. The core amino acid sequence may comprise of L or D stereoisomers or combination thereof. In some embodiments of the invention, the core amino acid sequence has at least 70%, 75%, 80%, 85%, 90%, 95% or 99% sequence identity to the amino acid sequences set forth in SEQ ID Nos: 12-22. The core amino acid sequence may comprise according to some embodiments, substitution, conservative amino acid substitutions, conservatively modified sequence variants, deletion, and/or insertion at one or more position or is in reverse order.

As used herein, in one embodiment the phrase "conservative amino acid substitutions" or the phrase "conservatively modified sequence variant" refer to trivial changes in amino acid sequence were one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified sequence variant", including where the alteration results in the substitution of an amino acid with a chemically similar amino acid (conservative amino acid substitutions). Conservative substitution tables providing functionally similar amino acids are well known in the art. Guidance concerning which amino acid changes are likely to be phenotypically silent can also be found in Bowie et al., 1990, Science 247: 1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

In some embodiments of the invention, the amino acid sequence of the member of the Cecropin family which forms the core amino acid of the peptide of the invention comprises 17-144 amino acids. In some embodiments of the invention, the amino acid sequence of the member of the Cecropin family comprises 20-140 amino acids. In some embodiments of the invention, the amino acid sequence of the member of the Cecropin family comprises 25-130 amino acids. In some embodiments of the invention, the amino acid sequence of the member of the Cecropin family comprises 20-40 amino acids. In some embodiments of the invention, the amino acid sequence of the member of the Cecropin family comprises 25-30 amino acids. In some embodiments of the invention, the amino acid sequence of the member of the Cecropin family comprises 20-50 amino acids. In some embodiments of the invention, the amino acid sequence of the member of the Cecropin family comprises 15-50 amino acids. In some embodiments of the invention, the amino acid sequence of the member of the Cecropin family comprises 20-70 amino acids. In some embodiments of the invention, the amino acid sequence of the member of the Cecropin family comprises 20-100 amino acids. In some embodiments of the invention, the peptide comprises a C-terminus group and/or an N terminus group wherein the C-terminus group and/or the N terminus group comprises one or more of cysteine, cysteine derivative, an amino acid sequence which contains cysteine or a group comprising a thiol moiety or any combination thereof.

In some embodiments of the invention, the c-terminus group and/or the N terminus group are each selected from the group consisting of cysteine, cysteine derivative, an amino acid sequence which contains cysteine or any other group comprising a thiol moiety. In some embodiments of the invention, the N-terminus group comprises the amino acid sequence methionine-cysteine, methionine-cysteine derivative, methionine derivative-cysteine or methionine derivative-cysteine derivative and the C-terminus group is cysteine or a cysteine derivative. In some embodiments of the invention, the C-terminus group comprises the amino acid sequence methionine-cysteine, methionine-cysteine derivative, methionine derivative-cysteine or methionine derivative-cysteine derivative and the N-terminus group is cysteine or a cysteine derivative.

In some embodiments of the invention, the N-terminus group and the C-terminus group are covalently bound so as to form a cyclic peptide. The covalent linkage may be a disulfide bond, an amide, lactam or peptide bond.

In some embodiments of the invention, the c-terminus group and the N terminus group are each selected from the group of L-amino acids, D-amino acids, non-natural amino acid or amino acid derivative.

In some embodiments of the invention, the peptide is self-assembled within a physiological membrane such that the intermolecular covalent linkage is formed between the N-terminus group of the peptide to the N-terminus or a C-terminus group of an additional identical peptide or wherein the intermolecular covalent linkage is formed between the C-terminus group of the peptide to the N-terminus or a C-terminus groups of an additional identical peptide.

In some embodiments of the invention, wherein the peptide is as set forth in SEQ ID Nos. 1-11. In some embodiments, the peptide is as set forth in SEQ ID. No. 6, which is also designated here OMN 6.

In some embodiments, the peptides of the invention are stabilized by an amide group added to the C-terminus group and or by an acetyl group to the N-terminus group. In some embodiments, the peptides of the invention are stabilized by any technique which is known in the art such as the addition of a non-proteinaceous or proteinaceous moiety.

In an embodiment of the invention, the non-proteinaceous is polyethylene glycol (PEG) or derivative thereof, polyvinyl pyrrolidone (PVP), albumin, divinyl ether, maleic anhydride copolymer (DIVEMA; and poly(styrene comaleic anhydride) (SMA), hyaluronic acid (HA), alginic acid (AA), polyhydroxyethyl methacrylate (Poly-HEMA), glyme or polyisopropylacrylamide or any combination thereof.

In one embodiment, this invention provides a functionally equivalent molecule that mimics the functional activity of any of the peptide or peptide variants provided in this invention. The term "functionally equivalent molecule" refers in the application to any compound such as but not restricted to peptidomimetic or stapled peptide. The functionally equivalent molecule may be obtained by retro-inverso or D-retro-enantiomer peptide technique, consisting of D-amino acids in the reversed sequence. The functionally equivalent molecule may be obtained by using amino acid derivative.

As used herein, in one embodiment, the term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NH-G(Sc)—C(0)-Q or —OC(0)G(Sc)-Q, wherein Q is —SR, —NRR or alkoxyl, R is hydrogen or alkyl, Sc is a side chain of a naturally occurring or non-naturally occurring amino acid and G is C1-C2 alkyl. In certain embodiments, G is Ci alkyl and Sc is selected from the group consisting of hydrogen, alkyl, heteroalkyl, arylalkyl and heteroarylalkyl.

As used herein, in one embodiment, the term "peptide" may be derived from a natural biological source, synthesized, or produced by recombinant technology. It may be generated in any manner, including by chemical synthesis. One or more of the amino acids may be modified, for example, by the addition of a chemical entity such as a carbohydrate group, a phosphate group, a farnesyl group, an isofamesyt group, a fatty acid group, an acyl group (e.g., acetyl group), a linker for conjugation, functionalization, or other known protecting/blocking groups.

As used herein, in one embodiment, the term "peptide" may be fragments, derivatives, analogs, or variants of the foregoing peptides, and any combination thereof. "Fragments of peptides", as that term or phrase is used herein, include proteolytic fragments, as well as deletion fragments. "Variants of peptides" include fragments and peptides with altered amino acid sequences due to amino acid substitutions, deletions, or insertions.

Variants may occur naturally or be non-naturally occurring. Examples include fusion proteins, peptides having one or more residues chemically derivatized by reaction of a functional side group, and peptides that contain one or more naturally occurring amino acid derivatives of the twenty standard amino acids. These modifications may also include the incorporation of D-amino acids, or other non-encoded amino-acids. In one embodiment, none of the modifications should substantially interfere with the desired biological activity of the peptide, fragment thereof. In another embodiment, modifications may alter a characteristic of the peptide, fragment thereof, for instance stability or half-life, without interfering with the desired biological activity of the peptide, fragment thereof. In one embodiment, as used herein the terms "peptide" and "protein" may be used interchangeably having all the same meanings and qualities.

In one embodiment, peptides of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the peptide of the present invention and fused cleavable moiety. In one embodiment, a fusion protein can be designed so that the peptide can be readily isolated by affinity chromatography; e.g., by immobilization on a column specific for the cleavable moiety. In one embodiment, a cleavage site is engineered between the peptide and the cleavable moiety and the peptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the peptide of the present invention is retrieved in a substantially pure form.

In one embodiment, the phrase "substantially pure" refers to a purity that allows for the effective use of the protein in the applications described herein.

In one embodiment, the peptide of the present invention can also be synthesized using in vitro expression systems. In one embodiment, in vitro synthesis methods are well known in the art and the components of the system are commercially available.

In one embodiment, a peptide of this invention is produced to synthetic process. In some embodiments the peptide is produced using recombinant DNA technology. A "recombinant" peptide, or protein refers to a peptide, or protein produced by recombinant DNA techniques; i.e., produced from cells transformed by an exogenous DNA construct encoding the desired peptide or protein.

In some embodiments, the recombinant peptides, fragments thereof or peptides are synthesized and purified; their therapeutic efficacy can be assayed either in vivo or in vitro. In one embodiment, the activities of the peptides of the present invention can be ascertained using various assays including inter-alia cell viability, survival of mice, and recovery of wounds.

In one embodiment, a peptide of this invention comprises at least 20 amino acids. In another embodiment, a peptide comprises at least 25 amino acids. In other embodiments, a peptide comprises at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids.

As used herein, in one embodiment, the terms "peptide" and "fragment" may be used interchangeably having all the same meanings and qualities. As used herein, in one embodiment the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein under.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several locations (2-3) at the same time.

Natural aromatic amino acids, Trp, Tyr and Phe, may be substituted for synthetic non-natural acids such as TIC, naphthylelanine (Nol), ring-methylated derivatives of Phe, halogenated derivatives of Phe or o-methyl-Tyr.

As used herein, in one embodiment the term "amino acid" refers to naturally occurring and synthetic α, β, γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration.

Alternatively, the amino acid can be a derivative of alanyl, valinyl, leuciny, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. As used herein, in one embodiment the phrase "Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant", including where the alteration results in the substitution of an amino acid with a chemically similar amino acid. Conservative substitution tables providing functionally similar amino acids are well known in the art. Guidance concerning which amino acid changes are likely to be phenotypically silent can also be found in Bowie et al., 1990, Science 247: 1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

In some embodiments, the peptide of the invention is an isolated peptide. As used herein, in one embodiment the term "isolated" means altered "by the hand of man" from its natural state; i.e., that, if it occurs in nature, it has been changed or removed from its original environment, or both.

The peptides of the invention may be assayed for example by an agarose dilution MIC assay, a broth dilution, time-kill assay, or equivalent methods. Antibiotic activity is measured as inhibition of growth or killing of a microorganism (e.g., bacteria, fungi).

According to another embodiment of the invention, under oxidative environment, e.g. as in infections, the cysteines in the carboxy- and amino-terminus of the peptide of the invention are covalently attached to one another, thus creating in some embodiments, a cyclic form of the peptide, which represents higher stability while maintaining the peptide's original biological activity or even an improved activity compared to the original form. In some embodiments, these peptides are used as an antibiotic medicament.

The invention also provides a method for expressing the novel cysteine harboring peptides from the Cecropin family in single cell heterologous expression systems. The method enables a large scale expression while avoiding rapid degradation by proteolysis activity.

According to some embodiments of the invention, there is provided a nucleic acid sequence encoding the peptide of any one of the sequences as set for in SEQ ID Nos. 1-11 or a vector comprising the nucleic acid sequence encoding the peptide of any one of the sequences as set for in SEQ ID Nos. 1-11.

A massive production of OMN's in heterologous expression system such as the yeast strains *Saccharomyces cerevisiae/Pichia pastoris* or compatible bacteria strains, serves in some embodiments of the invention to generate a 1 class of agents effective against a wide range of both Gram-positive and Gram-negative bacteria which overcome the problem of antibiotic resistance.

According to one method of the invention, the desired genes, such as, but not limited to, any of the peptides listed in Table 1, e.g. the OMN6 gene (SEQ ID NO:25), are identified, isolated, and cloned into a suitable vector after the addition of Cysteine codons to each of the carboxy- and amino-terminus of the genes. The vector is suitable for high-quantity expression of the target peptides, e.g. pPIC9K and pET28 plasmids, and are transformed into an acceptable target expression system, e.g. BL21, *Pichia pastoris, Saccharomyces cerevisiae* cells, etc.

Desired genes encoding proteins from the Cecropin family are genetically engineered to possess an even number of cysteines located at their carboxy and amino terminus. Table 1 provides a detailed list of several peptides of the Cecropin family, including their naive amino acid sequence and the added Cysteine and Methionine residues.

One method of the invention is the insertion of an ATG codon (encoding the methionine amino acid) to the 5' of mature Cecropin genes. When unmodified peptides are engineered and cysteine residues are inserted downstream of native ATG codon.

In another embodiment of the invention, the insertion of desired AMCP gene downstream to a region encoding for 6 histidine residues (His-Tag) is provided. A large number of compatible vectors suitable for this purpose are known to those of skill in the art. One example of the invention is the use of the vector pET28a, for the expression of the peptides in compatible bacterial expression system. The use the 6 histidine residues His-Tag is a well-known technique for isolation and purification of proteins from expression system cells.

The use of eukaryotic expression systems is commonly used for the production of foreign proteins. One example of such system is the methanoltrophic *Pichia pastoris* yeast strain. *P. pastoris* has been developed into an excellent host system for massive production of desired proteins. One of the advantages of using *P. pastoris* over *E. coli* bacterial cells is that the proteins of interest are usually folded correctly and secreted to the growth medium. Furthermore, *P. pastoris* does not have the endotoxin problem associated with bacteria especially when concerning antimicrobial peptides as required in this invention. Therefore, one embodiment of the invention is the insertion of OMN genes into pPIC9K, a *Pichia* Vector for multi-copy integration and secreted expression (Invitrogen). OMN gene of choice is cloned into said expression, resulting in pPIC9K-OMN (9.5 Kb). Cloning the OMN genes downstream to the AOX1 promoter verifies that their expression is under its regulation. For example, OMN gene containing ATG-TGC codons, encoding methionine and cysteine respectively, at the 5' of its naïve origin; and TGC-codon, encoding cysteine, at its 3'; results in the expression of desired cyclic peptides of the invention.

According to some embodiment of the invention, there is provided a method of overcoming inherent or acquired resistance of a microorganism to an antibiotic agent, comprising: contacting the microorganism to the peptide of the invention as described herein. The microorganism is, in some embodiments, *Escherichia coli, Klebsiella Pneumoniaea, Pseudomonas aeruginosa, Salmonella* serotype

*Typhi, Acinetobacter baumannii*, a member of Enterobacteriaceae spp., *Pseudomonas* spp. *Salmonella* spp., *Acinetobacter* spp. or any combination thereof, As used herein "inherent resistance" of a microorganism to an antibiotic agent refers to a natural resistance to the action of the agent even in the absence of prior exposure to the agent. (R. C. Moellering Jr., Principles of Anti-infective Therapy; In: Principles and Practice of Infectious Diseases, 4.sup.th Edition, Eds.; G. L. Mandell, J. E. Bennett, R. Dolin. Churchill Livingstone, New York USA, 1995, page 200).

As used herein, "acquired resistance" of a microorganism to an antibiotic agent refers to a resistance that is not inhibited by the normal achievable serum concentrations of a recommended antibiotic agent based on the recommended dosage. (NCCLS guidelines).

As used herein, "tolerance" of a microorganism to an antibiotic agent refers to when there is microstatic, rather than microcidal effect of the agent. Tolerance is measured by an MBC:MIC ratio greater than or equal to 32. (Textbook of Diagnostic Microbiology, Eds., C. R. Mahon and G. Manuselis, W.B. Saunders Co., Toronto Canada, 1995, page 92).

As noted above, this invention provides methods of treating infections caused by a microorganism, methods of killing a microorganism, and methods of enhancing the activity of an antibiotic agent. In particular, these methods are especially applicable when a microorganism is resistant to an antibiotic agent, by a mechanism, such as tolerance, inherent resistance, or acquired resistance. In this invention, infections are treated by administering a therapeutically effective dose of a cationic peptide alone or in combination with an antibiotic agent to a patient with an infection. Similarly, the combination can be contacted with a microorganism to effect killing.

In some embodiments of the invention, there is provided a method of disinfecting a wound comprising contacting the wound with the peptide or the pharmaceutical composition of the invention. The wound may be in some embodiments, a blister wound, a soft tissue wound, a cutaneous abscess, a surgical wound, a sutured laceration, a contaminated laceration, a burn wound, a decubitus ulcer, a stasis ulcer, a leg ulcer, a foot ulcer, a venous ulcer, a diabetic ulcer, an ischemic ulcer, a pressure ulcer, an oral infection, a periodontal disease, a partial thickness burn, or a full thickness burn.

In some embodiments of the invention, there is provided a method of treating an infection, the method comprising administering the peptide or the pharmaceutical composition of the invention to a subject in need thereof.

In some embodiments of the invention, the invention provides use of the peptide as described herein or a pharmaceutical composition comprising the same in the preparation of a medicament for treating an infection in a subject. The infection may be bacterial, viral- and/or fungal infection.

As used herein in the specification and in the claims section below, the term "treat" or "treating" and their derivatives includes substantially inhibiting or slowing a pathogen growth, or killing the same. The pathogen may be selected from bacteria, virus, parasite and pathologic fungi.

According to a method of the invention, the peptide of the invention should be used in an effective amount to treat infections in mammals. As used herein, "effective amount" means an amount necessary to achieve the desired result. For example, an effective amount of the peptides of the invention to remove a bacterial infection from a mammal within 3 days, 4 days, 5 days, 7 days or 10 days. The "effective amount" for purposes herein is that determined by such considerations as are known in the art. Effective doses may be extrapolated from dose-response curves derived from in vitro or animal model test systems. It is to be understood that the "effective amount" is dependent on the treated bacteria, the subject's physical condition, etc. Determination of optimal ranges of effective amounts of the active ingredient, is within the skill of the art.

In some embodiments of the invention, there is provided a pharmaceutical composition comprising the peptide of the invention. The pharmaceutical composition may be in a form of a liquid, cream, gel, paste, powder, emulsion, an ointment, a liniment, a lotion, a transdermal system, an injection fluid, a suspension, a patch film patch or spray. In some embodiments, the formulation is in a form of capsule or a tablet or designed for being injected. The composition may be administered in conjunction with one or more additional anti-inflammatory active agent.

According to an embodiment, the compositions of the present invention may be formulated for topical, oral, ocular or pulmonary (e.g. for inhalation) administration. Other formulations are described hereinbelow and are within the scope of the invention.

As used herein a "pharmaceutical composition" refers to a preparation of the active ingredients described herein with other chemical components such as physiologically suitable carriers and excipients. The purpose of the composition is to facilitate administration of the active ingredients (e.g., the peptides of the invention) to the subject.

As used herein the term "active ingredient" refers to the peptide compositions accountable for the intended biological effect (i.e., for treatment or prevention of an infection). In some embodiments, the term "active ingredient" refers to the antibiotic drug and in some embodiments, the term "active ingredient" refers to the antibiotic drug in combination with the peptide of the invention.

Hereinafter, the phrases "physiologically acceptable carrier" and "pharmaceutically acceptable carrier" which may be interchangeably used to refer to a carrier or a diluent that does not cause significant irritation to the subject and does not abrogate the biological activity and properties of the administered active ingredients. An adjuvant is included under these phrases.

Herein, the term "excipient" refers to an inert substance added to the composition (pharmaceutical composition or cosmetic composition) to further facilitate administration of an active ingredient of the present invention.

Techniques for formulation and administration of drugs may be found in "Remington's Pharmaceutical Sciences" Mack Publishing Co., Easton, Pa., latest edition, which is incorporated herein by reference.

Techniques for formulation and administration may be found in "Remington: The Science and Practice of Pharmacy" Twentieth Edition, Lippincott Williams & Wilkins, Philadelphia, Pa. (1995). For human or animal administration, preparations should meet sterility, pyrogenicity, general safety and purity standards comparable to those required by the FDA. Administration of the pharmaceutical formulation can be performed in a variety of ways, as described herein.

Another aspect of the present invention relates to a pharmaceutical composition including a pharmaceutically acceptable carrier and an active ingredient which is the peptide of the invention. The phrase "active ingredient" refers to any of the peptides, the fragments thereof, the functionally equivalent molecule that mimics the functional activity of the peptide, or a polynucleotide encoding a peptide according to the embodiments of the present invention. The pharmaceutical composition can contain one or more of the above-identified active ingredients of the present invention. Typically, the pharmaceutical composition of the present invention will include an active ingredient of the present invention, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent of the active ingredient. In some embodiments, the composition will contain from about 20 to 75 percent of an active ingredient and will further contain adjuvants, carriers and/or excipients. Determination of optimal ranges of effective amounts of the active ingredient is within the skill of the art. In some embodiments, the pharmaceutical composition may comprise about 0.01 to about 100 mg/kg body-weight of the peptide. In some embodiments, the pharmaceutical composition may comprise about 0.5 to about 100 mg/kg body-weight of the peptide. In some embodiments, the pharmaceutical composition may comprise about 100 to about 500 mg/kg body-weight of the peptide. In some embodiments, the pharmaceutical composition may comprise about 100 to about 300 mg/kg body-weight of the peptide. Treatment regimen for the administration of the peptide of the present invention can also be determined readily by those with ordinary skill in art. That is, the frequency of administration and size of the dose can be established by routine optimization.

In some embodiments, the pharmaceutical composition is in a form of a solid unit dosage form such as a capsule, tablet and the like, such as an ordinary gelatin type containing the active ingredient thereof of the present invention, and a carrier, for example, lubricants and inert fillers such as, lactose, sucrose, or cornstarch. In another embodiment, the active ingredient is tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate. The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, the active ingredient can be incorporated with excipients and used in the form of tablets, capsules, elixirs, suspensions, syrups, and the like.

The active ingredient of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

For use as aerosols, the active ingredient thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

When administering the active ingredient of the present invention, and pharmaceutical compositions thereof, they can be administered systemically or, alternatively, they can be administered directly to a specific site. Thus, administering can be accomplished in any manner effective for delivering the active ingredients thereof or the pharmaceutical compositions to the specific targeted cells. Exemplary modes of administration include, without limitation, administering the active ingredients thereof or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Toxicity and therapeutic efficacy of the peptides described herein can be determined by standard pharmaceutical procedures in cell cultures or experimental animals, e.g., by determining the IC50 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, for example, Fingl et al., 1975, in The Pharmacological Basis of Therapeutics, Ch. 1 p. 1, the contents of which are hereby incorporated by reference in their entirety).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, depend on the subject being treated, the severity of the affliction, the manner of administration, the judgment of the prescribing physician, and all other relevant factors. Determination of the exact dose to be administered is conducted by methods known to a person of skill in the art.

It is further understood that the active ingredient of the invention can be formulated or administered together with additional active ingredients as required to treat the condition of the patient.

Alternately, one may administer the composition in a local rather than systemic manner, for example, by injecting the composition including the active ingredient (and a physiologically acceptable carrier) directly into a tissue region of a patient (e.g. to the infected skin or into a healthy skin that surrounds the infected skin).

Suitable routes of administration of the compositions may, for example, include ocular (e.g., to the eye), topical (e.g., to a keratinous tissue, such as the skin, hair, nail, scalp), transdermal, subdermal, pulmonary and oral (e.g., by mouth) administrations.

According to an embodiment, the composition of the present invention is administered topically, pulmonary (e.g. via inhalation), orally or ocularly.

As used herein the phrase "dermal administration" refers to applying or spreading the composition of the present invention onto the surface of the body, i.e. skin, scalp, hair, nails and the like, preferably on the surface affected by the infection.

As used herein the phrase "transdermal administration" refers to administration of the compositions of the present invention across the skin for systemic administration (e.g. via transdermal patches or by transdermal implants). The transdermal administration is typically effected in close proximity to the site of infection, however, transdermal administration may be carried out in any anatomical location as see fit by one of ordinary skill in the art.

As used herein the phrase "subdermal administration" refers to administering the compositions of the present invention under the skin (i.e. completely buried in the skin, e.g. via subdermal implants). The subdermal administration is typically effected in close proximity to the site of the infection, however, subdermal administration may be carried out in any anatomical location as see fit by one of ordinary skill in the art.

Compositions of the present invention may be manufactured by processes well known in the art, e.g., by means of conventional mixing, dissolving, granulating, dragee-making, levigating, emulsifying, encapsulating, entrapping or lyophilizing processes.

Compositions for use in accordance with some embodiments of the invention thus may be formulated in conventional manner using one or more physiologically acceptable carriers comprising excipients and auxiliaries, which facilitate processing of the active ingredients into preparations which, can be used cosmetically or pharmaceutically. Proper formulation is dependent upon the route of administration chosen.

In addition, a dose can be formulated in tissue cultures systems (e.g. ex-vivo systems) or in animal models to achieve a desired concentration or titer. Such information can be used to more accurately determine useful doses in humans. For example, a therapeutically effective amount can be evaluated in-vivo by determining the level of inflammation before and after administration of the composition in a subject affected by an inflammatory state [e.g. by use of a blood test such as a complete blood count (CBC), by observation of skin wounds and so forth].

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in humans. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity of the condition (e.g., the area, depth and degree of the infection) and the responsiveness of the subject to treatment, dosing can be of a single or a plurality of administrations, with course of treatment lasting from several days to several weeks, several months or several years, or until cure is effected or diminution of the infection is achieved. Alternatively, the compositions are administered in order to prevent occurrence of an infection in a subject at risk of developing an infection (e.g. a subject suffering from a chronic inflammatory disease). The compositions may be administered for prolonged periods of time (e.g. several days, several weeks, several months or several years) as to prevent occurrence of an infection.

According to an embodiment of the present invention, the compositions of the present invention are administered at least once a day. According to another embodiment, the compositions are administered twice a day, three times a day or more.

According to an embodiment of the present invention, administering is effected chronically.

According to another embodiment, administering is effected for at least about 10 days, 12 days, 14 days, 16 days, 18 days, 21 days, 24 days, 27 days, 30 days, 60 days, 90 days or more.

The amount of a composition to be administered will, of course, be dependent on the subject being treated, the severity of the affliction, the manner of administration, the judgment of the prescribing physician, etc.

The compositions of the present invention may be formulated as a unit dosage form. In such form, the preparation is subdivided into unit doses containing appropriate quantities of the active ingredients such as for a single administration. The unit dosage form can be a packaged preparation, the package containing discrete quantities of preparation, for example, an ampule, a dispenser, an adhesive bandage, a non-adhesive bandage, a wipe, a baby wipe, a gauze, a pad and a sanitary pad.

Additional factors may be incorporated into the compositions of the present invention (i.e., plant extracts as described hereinabove). These include, but are not limited to, extracellular matrix components (e.g. vitronectin, laminin, collagen, elastin), growth factors (e.g. FGF 1, FGF 2, IGF 1, IGF 2, PDGF, EGF, KGF, HGF, VEGF, SDF-1, GM-CSF, CSF, G-CSF, TGF alpha, TGF beta, NGF and ECGF), growth factors [e.g. erythropoietin, fibroblast growth factor, franulocyte-colony stimulating factor (G-CSF) and granulocyte-macrophage colony stimulating factor (GM-CSF)], hormones (e.g., insulin, growth hormone (GH), CRH, Leptin, Prolactin and TSH), angiogenic factors (e.g., angiogenin and angiopoietin), coagulation and anticoagulation factors [e.g., Factor I, Factor XIII, tissue factor, calcium, vWF, protein C, protein S, protein Z, fibronectin, antithrombin, heparin, plasminogen, low molecular weight heparin (Clixan), high molecular weight kininogen (HMWK), prekallikrein, plasminogen activator inhibitor-1 (PAI1), plasminogen activator inhibitor-2 (PAI2), urokinase, thrombomoduline, tissue plasminogen activator (tPA), alpha 2-antiplasmin and Protein Z-related protease inhibitor (ZPI)], cytokine inhibitors (e.g. Cyclosporin A; Alpha-2-Macroglobulin, Pentamidine, Pentoxifylline, Dexamethasone), chemokine inhibitors (e.g. Peptide 3, NR58.3-14-3), enzymes (e.g. endoglycosidases, exoglycosidases, endonucleases, exonucleases, peptidases, lipases, oxidases, decarboxylases, hydrases, chondroitinase, chondroitinase ABC, chondroitinase AC, hyaluronidase, keratanase, heparanases, heparanase splice variance, collagenase, trypsin, catalases), neurotransmitters, neuropeptides (e.g. substance P), vitamins (e.g., D-biotin, Choline Chloride, Folic acid, Myo-inositol, Niacinamide, D-Pantothenic acid, Calcium salts, Pyridoxal.HCl, Pyrodixine.HCl, Riboflavin, Thiamine.HCl, Vitamin B12, vitamin E, vitamin C, vitamin D, vitamin B1-6, vitamin K, vitamin A and vitamin PP), carbohydrates (e.g. Mono/Di/Polysacharides including glucose, mannose, maltose and fructose), ions, chelators (e.g. Fe chelators, Ca chelators), antioxidants (e.g., Vitamin E, Quarcetin, superoxide scavengers, Superoxide dismutase, H2O2 scavengers, free radicals scavengers, Fe scavengers), fatty acids (e.g., Triglycerides, Phospholipids, Cholesterols, free fatty acids and non free fatty acids, fatty alcohol, Linoleic acid, oleic acid and lipoic acid), antibiotics (e.g., Penicillins, Cephalosporins and Tetracyclines), amino acids (e.g., essential and non essential (from A-Z) especially glutamine and arginine), salts (e.g., prurivat salts and sulfate salts), sulfates (e.g. Calcium Sulfate), steroids (e.g., androgens, estrogens, progestagens, glucocorticoids and mineralocorticoids), analgesics, anesthetics, anti-bacterial agents, anti-yeast agents, anti-fungal agents, anti-viral agents, pro-biotic agents, anti-protozal agents, anti-pruritic agents, anti-dermatitis agents, anti-emetics, anti-inflammatory agents, anti-hyperkeratolyic agents, antiperspirants, anti-seborrheic agents, antihistamine agents, hypoxia inducible factors (e.g. HIF-1 alpha and beta and HIF-2), catecholamines (e.g., Epinephrine and Norepinephrine), Nucleosides and Nucleotides (e.g., Purins and Pyrimidines), Prostaglandins (e.g. Prostaglandin E2), Leucotriens, Erythropoietins (e.g. Thrombopoietin), Proteoglycans (e.g. Heparan sulfate, keratan sulfate), Hydroxyapatites [e.g. Hydroxyapatite (Ca10(PO4)6(OH)2)], Haptoglobins (Hp1-1, Hp2-2 and Hp1-2), Superoxide dismutases (e.g. SOD 1/2/3), Nitric Oxides, Nitric Oxide donors (e.g. nitroprusside, Sigma Aldrich, St. Louis, Mo., USA, Glutathione peroxidases, Hydrating compounds (e.g. vasopressin), cells (e.g. Platelets), cell medium (e.g. M199, DMEM/F12, RPMI, Iscovs), serum (e.g. human serum, fetal calf serum, fetal bovine serum), buffers (e.g., HEPES, Sodium Bicarbonate), detergents (e.g., Tween), disinfectants, herbs, fruit extracts, vegetable extracts (e.g. cabbage, cucumber), flower extracts, additional plant extracts, flavinoids (e.g. pomegranate juice), spices, leafs (e.g. Green tea, Chamomile), Polyphenols (e.g. Red Wine), honey, lectins, microparticles, nanoparticles (lyposomes), micelles, calcium carbonate (CaCO3, e.g. precipitated calcium carbonate, ground/pulverized calcium carbonate, albacar, PCC, GCC), calcite, limestone, crushed marble, ground limestone, lime, and chalk (e.g. whiting chalk, champagne chalk, french chalk).

The present formulation may also contain ingredients, substances, elements and materials containing, hydrogen, alkyl groups, aryl groups, halo groups, hydroxy groups, alkoxy groups, alkylamino groups, dialkylamino groups, acyl groups, carboxyl groups, carboamido groups, sulfonamide groups, aminoacyl groups, amide groups, amine groups, nitro groups, organo selenium compounds, hydrocarbons, and cyclic hydrocarbons.

The present formulation may be combined with substances such as benzol peroxide, vasoconstrictors, vasodilatators, salicylic acid, retinoic acid, azelaic acid, lactic acid, glycolic acid, pyreuric acid, tannins, benzlidenecamphor and derivatives thereof, alpha hydroxyis, surfactants.

Compositions of some embodiments of the present invention may be bioconjugated to polyethylenglycol (e.g. PEG, SE-PEG) which preserves the stability (e.g., against protease activities) and/or solubility (e.g., within a biological fluid such as blood, digestive fluid) of the active ingredients (i.e. plant extract compositions of the present invention) while preserving their biological activity and prolonging its half-life.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion, a soap, a paste, an emulsion, a gel, a spray or an aerosol.

Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

EXAMPLES

Some bacteria develop resistance to antibiotics through the expression of specialized pumps that, upon activation, lead to an efflux of drugs from the bacteria cells. The concentration of the antibiotic drug cannot reach effective levels intracellularly and the resistant bacteria remain alive. This form of resistance can be overcome if the influx of the antibiotic drug exceeds the efflux created by the pumps, leading to effective concentration of the antibiotic drug inside the bacteria cells. OMN antimicrobial peptides in some embodiments, form pores in the membranes of bacteria, wherein such pores may increase the influx of any small-molecule-based antibiotic drug that is found in the surrounding media of the bacteria. This increased influx of the antibiotic drug may restore the effective concentration of the drug intracellularly and lead to the bacteria death.

Example 1

Combination of OMN6 and Kanamycin Exerts a Powerful Antimicrobial Effect

In order to evaluate and determine the effectivity of combining the antimicrobial peptide OMN6 with the antibiotic drug Kanamycin (KAN) on the growth of resistant bacteria, the following experiment was performed. Growth and inhibition of KAN resistant bacteria were monitored after co-treatment with KAN and OMN6.

FIG. 1 presents: *Salmonella* serotype *Typhimurium* (ATCC 700408), a Multi-Drug Resistant (MDR) strain of bacteria were cultured in the presence of either OMN6 or Kanamycin KAN. The bacteria were introduced into solutions of OMN6 (217 µg/ml) and KAN (3.75 µg/ml) that, in those concentrations, were previously shown to be non-effective when added alone. These concentrations of OMN6 alone or KAN alone did not inhibit bacterial growth and did not lead to bacterial death. The bacteria were then cultured in the presence of a combination of OMN6 and KAN, and then, were administered simultaneously in the same non-effective concentrations. The bacteria were incubated for 17-20 hours and the growth of the bacteria was continuously monitored via spectrophotometry at 600 nm (OD600). As bacterial growth progresses, OD600 values rise, and where the growth is inhibited OD600 values remain constant.

The results clearly show that stand-alone treatment with 3.75 µg/ml of KAN or 217 µg/ml of OMN6 did not inhibit bacterial growth effectively. At the end of the experiment significant bacterial growth was observed. In contrast, when a combination of OMN6 at 217 µg/ml together with KAN at 3.75 µg/ml was used, a complete and long-lasting antimicrobial effect was achieved and bacterial growth was significantly inhibited.

A Minimal Inhibitory Concentration (MIC) of OMN6 217 µg/ml+KAN 3.75 µg/ml, was determined for this co-treatment (FIG. 1).

This combination treatment can serve to lower the effective doses of antibiotic drugs as well as to lower the concentration of the peptides described herein that are needed for inhibiting the growth of bacteria. Moreover, bacteria strains that are resistant to drugs can be resensitized to the same drugs that they are no longer susceptible to using the combination of the peptide with the antibiotic drug. Thus, this co-treatment may facilitate the treatment of infections involving antibiotic resistant bacteria.

Example 2

A Combination of OMN11 and Imipenem Exerts a Powerful Antimicrobial Effect

In order to evaluate and determine the effectivity of combining the antimicrobial peptide OMN11 with the antibiotic drug Imipenem (IPM) on the growth of resistant bacteria the following experiment was performed. Growth and inhibition of IPM resistant bacteria were monitored after co-treatment with IPM and OMN11.

Figure 2:
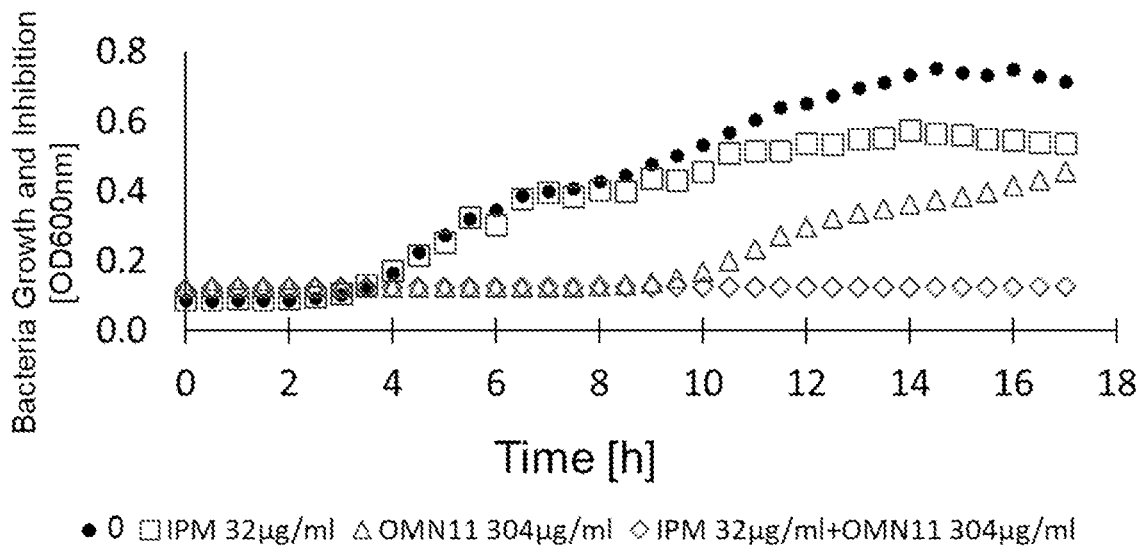
FIG. 2: *Salmonella* serotype *Typhimurium* (ATCC 700408) bacteria growth was monitored over 17.5 hours via absorbance at 600 nm. Bacteria growth or inhibition of growth is presented as absorbance values at 600 nm over time (OD600 nm). As the bacteria grow, OD values increase. The combination of OMN11 and the antibiotic drug Imipenem (IPM) exerted a powerful antimicrobial effect that is demonstrated by the low and constant OD values that represent bacterial death.

FIG. 2 presents: *Salmonella* serotype *Typhimurium* (ATCC 700408), a Multi-Drug Resistant (MDR) strain of bacteria, were cultured in the presence of either OMN11 or IPM.

The bacteria were introduced into solutions of OMN11 (304 µg/ml) and IPM (32 µg/ml) at concentrations that were previously shown to be non-effective when added alone. These concentrations of OMN11 alone or IPM alone did not inhibit bacterial growth and did not lead to bacterial death. The bacteria were then cultured in the presence of a combination of OMN11 and IPM, and administered simultaneously in the same non-effective concentrations shown above.

The bacteria were incubated for 17-20 hours and the growth of the bacteria was continuously monitored via spectrophotometry at 600 nm (OD600). As bacterial growth progresses, OD600 values rise, and where the growth is inhibited OD600 values remain constant.

The results clearly show that stand-alone treatment with 32 µg/ml of IPM or 304 µg/ml of OMN11 did not inhibit bacterial growth effectively. At the end of the experiment significant bacterial growth was observed.

In contrast, when a combination of OMN11 at 304 µg/ml together with IPM at 32 µg/ml was used, a complete and long-lasting antimicrobial effect was achieved and bacterial growth was significantly inhibited.

A Minimal Inhibitory Concentration (MIC) of OMN11 304 µg/ml+IPM 32 µg/ml, was determined for this co-treatment (FIG. 2).

This combination treatment can serve to lower the effective doses of antibiotic drugs as well as to lower the concentration of the peptides described herein that are needed for inhibiting the growth of bacteria. Moreover, bacteria strains that are resistant to drugs can be resensitized to the same drugs that they are no longer susceptible to using the combination of the peptide with the antibiotic drug. Thus, this co-treatment may facilitate the treatment of infections involving antibiotic resistant bacteria.

Example 3

A Combination of OMN6 and Ampicillin Exerts a Powerful Antimicrobial Effect on Two Separate Resistant Bacteria Strains In order to evaluate and determine the effectivity of combining the antimicrobial peptide OMN6 with the antibiotic drug Ampicillin (AMP) on the growth of resistant bacteria the following experiment was performed. Growth and inhibition of AMP resistant bacteria were monitored after co-treatment with AMP and OMN6.

Figure 3A:
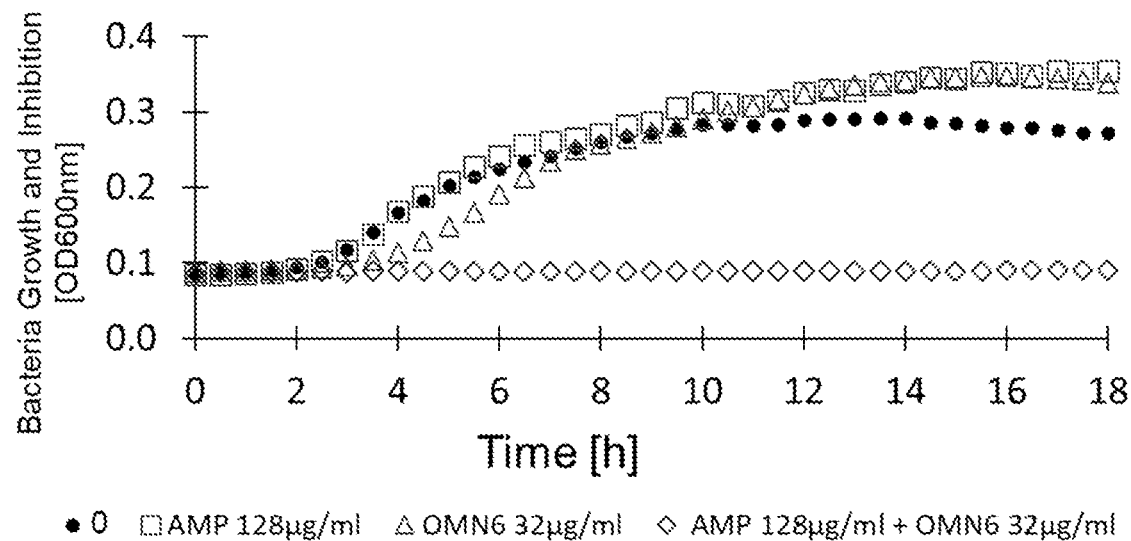
FIG. 3A: *Salmonella* serotype *Typhimurium* (ATCC 700408) bacteria growth monitored over 17.5 hours via absorbance at 600 nm. Bacteria growth or inhibition of growth is presented as absorbance values at 600 nm over time (OD600 nm). As the bacteria grow, OD values increase. The combination of OMN6 and the antibiotic drug Ampicillin (AMP) exerted a powerful antimicrobial effect that is demonstrated by the low and constant OD values that represent bacterial death.

FIG. 3A presents: *Salmonella* serotype *Typhimurium* (ATCC 700408), a Multi-Drug Resistant (MDR) strain of bacteria were cultured in the presence of OMN6 or AMP. The bacteria were introduced into solutions of either OMN6 (32 µg/ml) and AMP (128 µg/ml) at concentrations that were previously shown to be non-effective. These concentrations of OMN6 alone or AMP alone did not inhibit bacterial growth and did not lead to bacterial death. The bacteria were then cultured in the presence of a combination of OMN6 and AMP, and administered simultaneously in the same non-effective concentrations described above.

The bacteria were incubated for 17-20 hours and the growth of the bacteria was continuously monitored via spectrophotometry at 600 nm (OD600). As bacterial growth progresses, OD600 values rise, and where the growth is inhibited OD600 values remain constant.

The results clearly show that stand-alone treatment with 128 µg/ml of AMP or 32 µg/ml of OMN6 did not inhibit bacterial growth effectively. At the end of the experiment, significant bacterial growth was observed. In contrast, when a combination of OMN6 at 32 µg/ml together with AMP at 128 µg/ml was used, a complete and long-lasting antimicrobial effect was achieved and bacterial growth was significantly inhibited.

A Minimal Inhibitory Concentration (MIC) of OMN6 32 µg/ml+AMP 128 µg/ml, was determined for this co-treatment (FIG. 3A).

Figure 3B:
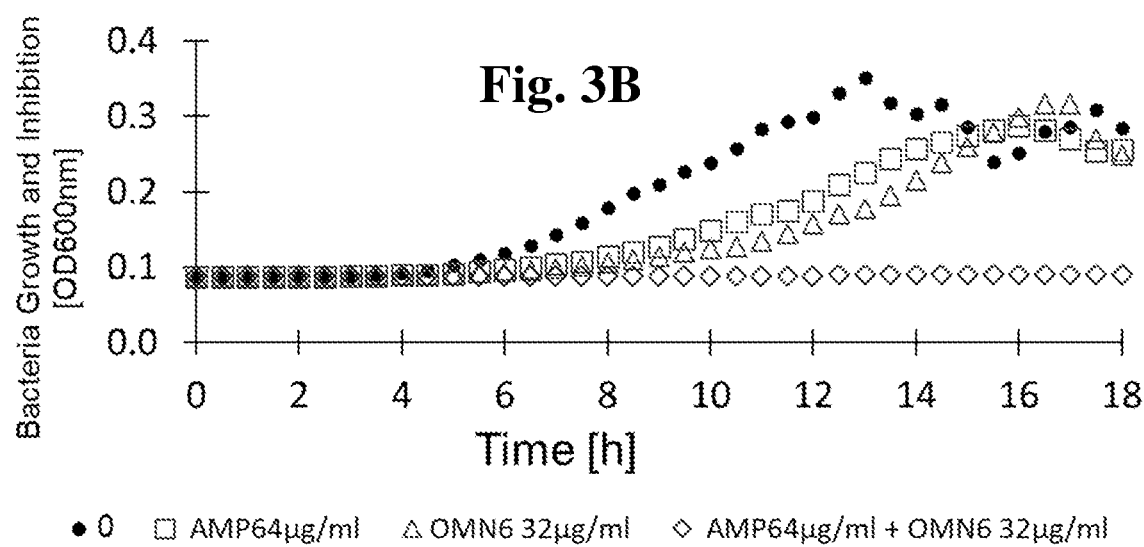
FIG. 3B: *Pseudomonas aeruginosa* (ATCC BAA-2110) bacteria growth was monitored over 17.5 hours via absorbance at 600 nm. Bacteria growth or inhibition of growth is presented as absorbance values at 600 nm over time (OD600 nm). As the bacteria grow, OD values increase. The combination of OMN6 and the antibiotic drug Ampicillin (AMP) exerted a powerful antimicrobial effect that is demonstrated by the low and constant OD values that represent bacterial death.

FIG. 3B presents: *Pseudomonas aeruginosa* (ATCC BAA-2110), a Multi-Drug Resistant (MDR) strain of bacteria were cultured in the presence of either OMN6 or AMP. The bacteria were introduced into solutions of OMN6 (32 µg/ml) and AMP (64 µg/ml) at concentrations that were previously shown to be non-effective when added alone. These concentrations of OMN6 alone or AMP alone did not inhibit bacterial growth and did not lead to bacterial death. The bacteria were then cultured in the presence of a co-treatment with a combination of OMN6 and AMP, and administered simultaneously, in the same non-effective concentrations described above.

The bacteria were incubated for 17-20 hours and the growth of the bacteria was continuously monitored via spectrophotometry at 600 nm (OD600). As bacterial growth progresses, OD600 values rise, and where the growth is inhibited OD600 values remain constant.

The results clearly show that stand-alone treatment with 128 µg/ml of AMP or 32 µg/ml of OMN6 did not inhibit bacterial growth effectively. At the end of the experiment, significant bacterial growth was observed. In contrast, when a combination of OMN6 at 32 µg/ml together with AMP at 64 µg/ml was used, a complete and long-lasting antimicrobial effect was achieved and bacterial growth was significantly inhibited.

A Minimal Inhibitory Concentration (MIC) of OMN6 32 μg/ml+AMP 64 μg/ml, was determined for this co-treatment (FIG. 3B).

This combination treatment can serve to lower the effective doses of antibiotic drugs as well as to lower the concentration of the peptides described herein that are needed for inhibiting the growth of bacteria. Moreover, bacteria strains that are resistant to drugs can be resensitisized to the same drugs that they are no longer susceptible to using the combination of the peptide with the antibiotic drug. Thus, this co-treatment may facilitate the treatment of infections involving antibiotic resistant bacteria.

Example 4

A Combination of OMN6 and Tetracycline Exerts a Powerful Antimicrobial Effect

In order to evaluate and determine the effectivity of combining the antimicrobial peptide OMN11 with the antibiotic drug Tetracycline (TET) on the growth of resistant bacteria, the following experiment was performed. Growth and inhibition of IPM resistant bacteria were monitored after co-treatment with IPM and OMN11.

FIG. 4 presents: *Salmonella* serotype *Typhimurium* (ATCC 700408), a Multi-Drug Resistant (MDR) strain of bacteria were cultured in the presence of OMN6 or TET.

The bacteria were introduced into solutions of OMN6 (32 μg/ml) and TET (16 μg/ml) at concentrations that were previously shown to be non-effective when administered alone. These concentrations of OMN6 alone or TET alone did not inhibit bacterial growth and did not lead to bacterial death. The bacteria were then cultured in the presence of a co-treatment with a combination of OMN6 and AMP, and administered simultaneously, in the same non-effective concentrations described above.

The bacteria were incubated for 17-20 hours and the growth of the bacteria was continuously monitored via spectrophotometry at 600 nm (OD600). As bacterial growth progresses, OD600 values rise, and where the growth is inhibited OD600 values remain constant.

The results clearly show that stand-alone treatment with 16 μg/ml of TET or 32 μg/ml of OMN6 did not inhibit bacterial growth effectively. At the end of the experiment significant bacterial growth was observed.

In contrast, when a combination of OMN6 at 32 μg/ml together with TET at 16 μg/ml was used, a complete and long-lasting antimicrobial effect was achieved and bacterial growth was significantly inhibited.

A Minimal Inhibitory Concentration (MIC) of OMN6 32 μg/ml+TET 162 μg/ml, was determined for this co-treatment (FIG. 4).

This combination treatment can serve to lower the effective doses of antibiotic drugs as well as to lower the concentration of the peptides described herein that are needed for inhibiting the growth of bacteria. Moreover, bacteria strains that are resistant to drugs can be resensitisized to the same drugs that they are no longer susceptible to using the combination of the peptide with the antibiotic drug. Thus, this co-treatment may facilitate the treatment of infections involving antibiotic resistant bacteria.

The combined results presented above demonstrate that when bacteria develop resistance to a specific drug, this drug is no longer effective even at high concentrations. Thus, such a drug can no longer be used for therapeutic purposes as it has lost its ability to control the growth of the resistant bacteria. In cases where an antibiotic drug is no longer effective against a resistant strain of bacteria, a combination of this drug with one of the peptides of the invention and in particular, those shown in Seq ID Nos. 1-11, can restore the ability of the drug to combat resistant bacteria.

What is claimed is:

1. A method of overcoming inherent or acquired resistance of a microorganism to an antibiotic agent, or of treating an infection comprising administering to a subject in need a combination of:
   a) a cyclic peptide according to the sequence as set forth in SEQ ID No. 6; and
   b) an antibiotic drug.

2. The method of claim 1, wherein the peptide and the antibiotic drug are administered simultaneously or consecutively.

3. The method of claim 1, wherein the microorganism is *Escherichia coli, Klebsiella Pneumoniaea, Pseudomonas aeruginosa, Salmonella* serotype *Typhi, Acinetobacter baumannii*, a member of Enterobacteriaceae spp., *Pseudomonas* spp. *Salmonella* spp., or *Acinetobacter* spp., or any combination thereof.

4. A method of disinfecting a wound comprising contacting the wound with a combination of:
   a) a cyclic peptide according to the sequence as set forth in SEQ ID No. 6; and
   b) an antibiotic drug.

5. The method of claim 4, wherein the wound is a blister wound, a soft tissue wound, a cutaneous abscess, a surgical wound, a sutured laceration, a contaminated laceration, a burn wound, a decubitus ulcer, a stasis ulcer, a leg ulcer, a foot ulcer, a venous ulcer, a diabetic ulcer, an ischemic ulcer, a pressure ulcer, an oral infection, a periodontal disease, a partial thickness burn, or a full thickness burn.

6. A pharmaceutical composition comprising a combination of:
   a) a cyclic peptide according to the sequence as set forth in SEQ ID No. 6; and
   b) an antibiotic drug.

7. A method according to claim 1, wherein the antibiotic drug is consisting of one or more of the following groups: Aminoglycoside, Ansamycin, Glycopeptide, Lincosamide, Macrolide, Monobactam, Nitrofuran, Oxazolidinone, Quinolone/Fluoroquinolone, Sulfonamide and Tetracycline.

8. A method according to claim 4, wherein the antibiotic drug is consisting of one or more of the following groups: Aminoglycoside, Ansamycin, Glycopeptide, Lincosamide, Macrolide, Monobactam, Nitrofuran, Oxazolidinone, Quinolone/Fluoroquinolone, Sulfonamide and Tetracycline.

9. A pharmaceutical composition according to claim 6, wherein the antibiotic drug is consisting of one or more of the following groups: Aminoglycoside, Ansamycin, Glycopeptide, Lincosamide, Macrolide, Monobactam, Nitrofuran, Oxazolidinone, Quinolone/Fluoroquinolone, Sulfonamide and Tetracycline.

* * * * *